United States Patent
Yeh et al.

(10) Patent No.: US 8,603,118 B2
(45) Date of Patent: Dec. 10, 2013

(54) TISSUE REPAIR SYSTEM

(75) Inventors: Jack Y. Yeh, North Potomac, MD (US); Mohit K. Bhatnagar, Potomac, MD (US); James A. Sack, Elverson, PA (US)

(73) Assignee: JMEA Corporation, Rockville, MD (US)

( * ) Notice: Subject to any disclaimer, the term of this patent is extended or adjusted under 35 U.S.C. 154(b) by 0 days.

(21) Appl. No.: 13/473,340

(22) Filed: May 16, 2012

(65) Prior Publication Data

US 2012/0232586 A1      Sep. 13, 2012

Related U.S. Application Data

(62) Division of application No. 12/564,323, filed on Sep. 22, 2009, now Pat. No. 8,211,126.

(51) Int. Cl.
*A61B 17/122* (2006.01)

(52) U.S. Cl.
USPC ............ 606/151; 606/142; 606/215; 606/232

(58) Field of Classification Search
USPC ......... 606/139, 142, 143, 151, 157, 158, 221, 606/232, 215
See application file for complete search history.

(56) References Cited

U.S. PATENT DOCUMENTS

| | | | |
|---|---|---|---|
| 2,881,762 A * | 4/1959 | Lowrie | 29/564 |
| 3,875,595 A | 4/1975 | Froning | |
| 4,006,747 A | 2/1977 | Kronenthal et al. | |
| 4,038,987 A * | 8/1977 | Komiya | 606/142 |
| 4,235,238 A * | 11/1980 | Ogiu et al. | 606/145 |
| 4,394,864 A * | 7/1983 | Sandhaus | 128/843 |
| 4,448,194 A | 5/1984 | DiGiovanni et al. | |
| 4,471,181 A | 9/1984 | Dennison | |
| 4,533,076 A | 8/1985 | Bourque | |
| 4,573,448 A | 3/1986 | Kambin | |
| 4,621,639 A | 11/1986 | Transue et al. | |
| 4,705,040 A | 11/1987 | Mueller et al. | |
| 4,724,840 A | 2/1988 | McVay et al. | |
| 4,873,976 A | 10/1989 | Schreiber | |
| 4,877,172 A | 10/1989 | Franklin et al. | |

(Continued)

FOREIGN PATENT DOCUMENTS

| | | |
|---|---|---|
| FR | 2651113 | 3/1991 |
| WO | 02058599 | 8/2002 |
| WO | 2006118930 | 11/2006 |

OTHER PUBLICATIONS

International Search Report and Written Opinion mailed Apr. 23, 2008 in PCT Application No. PCT/US2006/015960.

(Continued)

*Primary Examiner* — Kathleen Holwerda
(74) *Attorney, Agent, or Firm* — Plumsea Law Group, LLC

(57) ABSTRACT

A tissue repair system is disclosed. The tissue repair system can include a prosthesis with a first end portion, a second end portion and an intermediate portion disposed therebetween. The first end portion can engage the second end portion when installed to retain tissue in a desired configuration. The tissue repair system can also include a delivery device configured to implant and fasten the prosthesis to repair imperfections in tissue or retain tissue in a desired configuration. The delivery device may be configured to fasten the first end portion and second end portion of the prosthesis on a distal portion of the tissue.

24 Claims, 9 Drawing Sheets

(56) References Cited

U.S. PATENT DOCUMENTS

| | | |
|---|---|---|
| 4,884,572 A | 12/1989 | Bays et al. |
| 4,950,285 A | 8/1990 | Wilk |
| 4,997,436 A | 3/1991 | Oberlander |
| 5,002,562 A | 3/1991 | Oberlander |
| 5,085,661 A | 2/1992 | Moss |
| 5,154,189 A | 10/1992 | Oberlander |
| 5,192,326 A | 3/1993 | Bao et al. |
| 5,236,440 A | 8/1993 | Hlavacek |
| 5,281,230 A | 1/1994 | Heidmueller |
| 5,290,296 A | 3/1994 | Phillips |
| 5,290,297 A | 3/1994 | Phillips |
| 5,395,317 A | 3/1995 | Kambin |
| 5,403,346 A * | 4/1995 | Loeser ............ 606/228 |
| 5,423,857 A | 6/1995 | Rosenman et al. |
| 5,425,489 A | 6/1995 | Shichman et al. |
| 5,439,464 A | 8/1995 | Shapiro |
| 5,439,479 A | 8/1995 | Shichman et al. |
| 5,465,895 A | 11/1995 | Knodel et al. |
| 5,470,337 A | 11/1995 | Moss |
| 5,500,000 A | 3/1996 | Feagin et al. |
| 5,527,321 A | 6/1996 | Hinchliffe |
| 5,540,704 A | 7/1996 | Gordon et al. |
| 5,549,679 A | 8/1996 | Kuslich |
| 5,591,206 A | 1/1997 | Moufarrege |
| 5,601,571 A | 2/1997 | Moss |
| 5,632,433 A | 5/1997 | Grant et al. |
| 5,643,319 A | 7/1997 | Green et al. |
| 5,653,928 A | 8/1997 | Schnipke |
| 5,716,416 A | 2/1998 | Lin |
| 5,817,113 A | 10/1998 | Gifford, III et al. |
| 5,827,298 A | 10/1998 | Hart et al. |
| 5,836,147 A | 11/1998 | Schnipke |
| 5,843,084 A | 12/1998 | Hart et al. |
| 5,860,990 A | 1/1999 | Nobles et al. |
| 5,931,855 A | 8/1999 | Buncke |
| 5,941,439 A | 8/1999 | Kammerer et al. |
| 5,954,747 A | 9/1999 | Clark |
| 5,972,005 A | 10/1999 | Stalker et al. |
| 5,976,186 A | 11/1999 | Bao et al. |
| 5,980,504 A | 11/1999 | Sharkey et al. |
| 5,993,475 A | 11/1999 | Lin et al. |
| 5,997,552 A | 12/1999 | Person et al. |
| 6,010,513 A | 1/2000 | Tormala et al. |
| 6,039,753 A | 3/2000 | Meislin |
| 6,074,395 A | 6/2000 | Trott et al. |
| 6,099,514 A | 8/2000 | Sharkey et al. |
| 6,110,210 A | 8/2000 | Norton et al. |
| 6,126,670 A | 10/2000 | Walker et al. |
| 6,126,682 A | 10/2000 | Sharkey et al. |
| 6,146,387 A | 11/2000 | Trott et al. |
| 6,183,518 B1 | 2/2001 | Ross et al. |
| 6,190,401 B1 | 2/2001 | Green et al. |
| 6,206,921 B1 | 3/2001 | Guagliano et al. |
| 6,206,923 B1 | 3/2001 | Boyd et al. |
| 6,241,747 B1 | 6/2001 | Ruff |
| 6,245,107 B1 | 6/2001 | Ferree |
| 6,264,659 B1 | 7/2001 | Ross et al. |
| 6,270,517 B1 | 8/2001 | Brotz |
| 6,280,475 B1 | 8/2001 | Bao et al. |
| 6,290,715 B1 | 9/2001 | Sharkey et al. |
| 6,306,156 B1 | 10/2001 | Clark |
| 6,318,553 B1 | 11/2001 | Deschenes |
| 6,322,563 B1 | 11/2001 | Cummings et al. |
| 6,332,894 B1 | 12/2001 | Stalcup et al. |
| 6,387,113 B1 | 5/2002 | Hawkins et al. |
| 6,387,130 B1 | 5/2002 | Stone et al. |
| 6,395,031 B1 | 5/2002 | Foley et al. |
| 6,402,750 B1 | 6/2002 | Atkinson et al. |
| 6,425,919 B1 | 7/2002 | Lambrecht |
| 6,427,895 B1 | 8/2002 | Deschenes |
| 6,428,576 B1 | 8/2002 | Haldimann |
| 6,443,988 B2 | 9/2002 | Felt et al. |
| 6,446,854 B1 | 9/2002 | Remiszewski et al. |
| 6,482,235 B1 | 11/2002 | Lambrecht et al. |
| 6,491,724 B1 | 12/2002 | Ferree |
| 6,497,707 B1 | 12/2002 | Bowman et al. |
| 6,508,839 B1 | 1/2003 | Lambrecht et al. |
| 6,517,568 B1 | 2/2003 | Sharkey et al. |
| 6,530,933 B1 | 3/2003 | Yeung et al. |
| 6,551,343 B1 | 4/2003 | Tormala et al. |
| 6,562,033 B2 | 5/2003 | Shah et al. |
| 6,564,939 B1 | 5/2003 | Deschenes et al. |
| 6,569,369 B2 | 5/2003 | Shilale et al. |
| 6,579,291 B1 | 6/2003 | Keith et al. |
| 6,592,625 B2 | 7/2003 | Cauthen |
| 6,596,008 B1 | 7/2003 | Kambin |
| 6,596,014 B2 | 7/2003 | Levinson et al. |
| 6,599,310 B2 | 7/2003 | Leung et al. |
| 6,602,291 B1 | 8/2003 | Ray et al. |
| 6,638,276 B2 | 10/2003 | Sharkey et al. |
| 6,676,678 B2 | 1/2004 | Gifford, III et al. |
| 6,682,535 B2 | 1/2004 | Hoogland |
| 6,685,077 B1 | 2/2004 | Davignon et al. |
| 6,689,125 B1 | 2/2004 | Keith et al. |
| 6,692,499 B2 | 2/2004 | Tormala et al. |
| 6,709,442 B2 | 3/2004 | Miller et al. |
| 6,719,763 B2 | 4/2004 | Chung et al. |
| 6,726,685 B2 | 4/2004 | To et al. |
| 6,733,496 B2 | 5/2004 | Sharkey et al. |
| 6,733,531 B1 | 5/2004 | Trieu |
| 6,736,815 B2 | 5/2004 | Ginn |
| 6,746,685 B2 | 6/2004 | Williams |
| 6,755,843 B2 | 6/2004 | Chung et al. |
| 6,776,784 B2 | 8/2004 | Ginn |
| 6,779,701 B2 | 8/2004 | Bailly et al. |
| 6,805,695 B2 | 10/2004 | Keith et al. |
| 6,848,152 B2 | 2/2005 | Genova et al. |
| 7,004,970 B2 | 2/2006 | Cauthen, III et al. |
| 7,052,516 B2 | 5/2006 | Cauthen, III et al. |
| 7,056,330 B2 | 6/2006 | Gayton |
| 7,189,235 B2 | 3/2007 | Cauthen |
| 7,338,502 B2 * | 3/2008 | Rosenblatt ............ 606/139 |
| 7,547,326 B2 | 6/2009 | Bhatnagar et al. |
| 7,608,108 B2 | 10/2009 | Bhatnagar et al. |
| 7,632,313 B2 | 12/2009 | Bhatnagar et al. |
| 8,070,818 B2 | 12/2011 | Bhatnagar et al. |
| 8,177,847 B2 | 5/2012 | Bhatnagar et al. |
| 2001/0004710 A1 | 6/2001 | Felt et al. |
| 2001/0010021 A1 | 7/2001 | Boyd et al. |
| 2002/0019626 A1 | 2/2002 | Sharkey et al. |
| 2002/0019636 A1 | 2/2002 | Ogilvie et al. |
| 2002/0022830 A1 | 2/2002 | Sharkey et al. |
| 2002/0026195 A1 | 2/2002 | Layne et al. |
| 2002/0068974 A1 | 6/2002 | Kuslich et al. |
| 2002/0111688 A1 | 8/2002 | Cauthen |
| 2002/0120337 A1 | 8/2002 | Cauthen |
| 2002/0123807 A1 | 9/2002 | Cauthen, III |
| 2002/0147461 A1 | 10/2002 | Aldrich et al. |
| 2002/0147479 A1 | 10/2002 | Aldrich |
| 2002/0147496 A1 | 10/2002 | Belef et al. |
| 2002/0147497 A1 | 10/2002 | Belef et al. |
| 2002/0151976 A1 | 10/2002 | Foley et al. |
| 2002/0151979 A1 | 10/2002 | Lambrecht et al. |
| 2002/0151980 A1 | 10/2002 | Cauthen |
| 2002/0156530 A1 | 10/2002 | Lambrecht et al. |
| 2002/0156531 A1 | 10/2002 | Felt et al. |
| 2002/0165542 A1 | 11/2002 | Ferree |
| 2002/0173851 A1 | 11/2002 | McKay |
| 2002/0183848 A1 | 12/2002 | Ray et al. |
| 2002/0189622 A1 | 12/2002 | Cauthen, III et al. |
| 2002/0198599 A1 | 12/2002 | Haldimann |
| 2003/0009227 A1 | 1/2003 | Lambrecht et al. |
| 2003/0014118 A1 | 1/2003 | Lambrecht et al. |
| 2003/0014177 A1 | 1/2003 | Herb et al. |
| 2003/0028251 A1 | 2/2003 | Mathews |
| 2003/0040796 A1 | 2/2003 | Ferree |
| 2003/0069641 A1 | 4/2003 | Reuter et al. |
| 2003/0074075 A1 | 4/2003 | Thomas, Jr. et al. |
| 2003/0078579 A1 | 4/2003 | Ferree |
| 2003/0082169 A1 | 5/2003 | Boyd |
| 2003/0083642 A1 | 5/2003 | Boyd et al. |
| 2003/0093155 A1 | 5/2003 | Lambrecht et al. |
| 2003/0114930 A1 | 6/2003 | Lim et al. |
| 2003/0120345 A1 | 6/2003 | Cauthen |

(56) References Cited

U.S. PATENT DOCUMENTS

| | | |
|---|---|---|
| 2003/0125748 A1 | 7/2003 | Li et al. |
| 2003/0125807 A1 | 7/2003 | Lambrecht et al. |
| 2003/0153976 A1 | 8/2003 | Cauthen, III et al. |
| 2003/0158604 A1 | 8/2003 | Cauthen, III et al. |
| 2003/0163200 A1 | 8/2003 | Cauthen |
| 2003/0167055 A1 | 9/2003 | Kolata et al. |
| 2003/0181964 A1 | 9/2003 | Sharkey et al. |
| 2003/0181983 A1 | 9/2003 | Cauthen |
| 2003/0187445 A1 | 10/2003 | Keith et al. |
| 2003/0187507 A1 | 10/2003 | Cauthen |
| 2003/0187508 A1 | 10/2003 | Cauthen |
| 2003/0191436 A1 | 10/2003 | Horvers |
| 2003/0195514 A1 | 10/2003 | Trieu et al. |
| 2003/0195628 A1 | 10/2003 | Bao et al. |
| 2003/0195630 A1 | 10/2003 | Ferree |
| 2003/0199979 A1 | 10/2003 | McGuckin, Jr. |
| 2003/0199984 A1 | 10/2003 | Trieu |
| 2003/0220649 A1 | 11/2003 | Bao et al. |
| 2003/0220690 A1 | 11/2003 | Cauthen, III |
| 2003/0220693 A1 | 11/2003 | Cauthen, III |
| 2003/0220694 A1 | 11/2003 | Cauthen, III |
| 2003/0220695 A1 | 11/2003 | Sevrain |
| 2004/0002746 A1 | 1/2004 | Ryan et al. |
| 2004/0002760 A1 | 1/2004 | Boyd et al. |
| 2004/0002763 A1 | 1/2004 | Phillips et al. |
| 2004/0002764 A1 | 1/2004 | Gainor et al. |
| 2004/0010317 A1 | 1/2004 | Lambrecht et al. |
| 2004/0019381 A1 | 1/2004 | Pflueger |
| 2004/0024463 A1 | 2/2004 | Thomas, Jr. et al. |
| 2004/0024465 A1 | 2/2004 | Lambrecht et al. |
| 2004/0030392 A1 | 2/2004 | Lambrecht et al. |
| 2004/0034429 A1 | 2/2004 | Lambrecht et al. |
| 2004/0039392 A1 | 2/2004 | Trieu |
| 2004/0044412 A1 | 3/2004 | Lambrecht et al. |
| 2004/0059417 A1 | 3/2004 | Smith et al. |
| 2004/0059418 A1 | 3/2004 | McKay et al. |
| 2004/0064023 A1 | 4/2004 | Ryan et al. |
| 2004/0068268 A1 | 4/2004 | Boyd et al. |
| 2004/0073308 A1 | 4/2004 | Kuslich et al. |
| 2004/0083002 A1 | 4/2004 | Belef et al. |
| 2004/0092933 A1 | 5/2004 | Shaolian et al. |
| 2004/0092945 A1 | 5/2004 | Ferree |
| 2004/0097924 A1 | 5/2004 | Lambrecht et al. |
| 2004/0097980 A1 | 5/2004 | Ferree |
| 2004/0102774 A1 | 5/2004 | Trieu |
| 2004/0267309 A1 | 12/2004 | Garvin |
| 2005/0055027 A1 | 3/2005 | Yeung et al. |
| 2005/0070924 A1 | 3/2005 | Schaller et al. |
| 2006/0247643 A1 | 11/2006 | Bhatnagar et al. |
| 2007/0088438 A1 | 4/2007 | Cauthen, III et al. |
| 2007/0100348 A1 | 5/2007 | Cauthen, III et al. |
| 2007/0100354 A1 | 5/2007 | Cauthen, III et al. |
| 2007/0149987 A1* | 6/2007 | Wellman et al. ............... 606/148 |
| 2007/0185497 A1 | 8/2007 | Cauthen et al. |
| 2009/0118734 A1 | 5/2009 | Bhatnagar et al. |
| 2011/0071548 A1 | 3/2011 | Yeh et al. |

OTHER PUBLICATIONS

International Search Report and the Written Opinion of the International Searching Authority, mailed Jan. 17, 2011 in PCT Application No. PCT/US2010/049613.

Notification Concerning Transmittal of International Preliminary Report on Patentability, mailed Apr. 9, 2009 in PCT Application No. PCT/US2006/015960.

Office Action from U.S. Appl. No. 11/934,737, mailed May 11, 2011.

Response to Office Action filed on Jul. 25, 2011 for U.S. Appl. No. 11/934,737.

Decision Granting Petition from U.S. Appl. No. 11/934,737, mailed Aug. 24, 2011.

Final Office Action from U.S. Appl. No. 11/934,737, mailed Dec. 20, 2011.

Amendment Accompanying Request for Continued Examination filed on May 21, 2012 for U.S. Appl. No. 11/934,737.

Request for Continued Examination filed May 21, 2012 for U.S. Appl. No. 11/934,737.

Office Action from U.S. Appl. No. 12/413,113, mailed Jun. 30, 2011.

Response to Office Action filed on Sep. 22, 2011 for U.S. Appl. No. 12/413,113.

Notice of Allowance from U.S. Appl. No. 12/413,113 mailed Oct. 7, 2011.

Notice of Allowance from U.S. Appl. No. 12/612,970 mailed Sep. 28, 2011.

Request for Continued Examination filed on Nov. 2, 2011 for U.S. Appl. No. 12/612,970.

Notice of Allowance from U.S. Appl. No. 12/612,970 mailed Dec. 16, 2011.

* cited by examiner

TISSUE REPAIR SYSTEM

CROSS REFERENCE TO RELATED APPLICATION

This application is a division of U.S. Patent Publication No. US 2011/0071548 (U.S. patent application Ser. No. 12/564,323, filed Sep. 22, 2009), now U.S. Pat. No. 8,211,126, issued Jul. 3, 2012, which is herein incorporated by reference in its entirety.

BACKGROUND OF THE INVENTION

1. Field of the Invention

The present invention relates generally to implantation systems and in particular to an implantation system for tissue repair.

2. Description of Related Art

Currently, closure prostheses for repairing tears, cuts, holes or other imperfections in tissue operate by inserting two ends of a closure prosthesis into the tissue simultaneously, in effect "stapling" the prosthesis into place. Current methods for implanting closure prostheses lack provisions to increase precision in the delivery of the prosthesis and to increase control of implantation.

Chung et al. (U.S. Pat. No. 6,755,843) teaches an endoscopic suturing device. The suturing device includes a single needle that is configured to penetrate through tissue.

Hinchliffe (U.S. Pat. No. 5,527,321) teaches an instrument for closing puncture wounds. Hinchliffe teaches a device, including two pivoting needles. The tip of the device is inserted into a puncture wound. Following this, the needles are rotated from outside of the housing into tissue. At this point, the needles are caught within a latch member. Then, the device is pulled back through the puncture wound, along with the needles, so that the suture is pulled through the wound exiting at the open surface of the skin. The suture is then cut away from the needles and tied off.

Gordon et al. (U.S. Pat. No. 5,540,704) teaches an endoscopic suture system. Gordon teaches a pair of needles that are guided by a guiding track through tissue adjacent to a wound. Initially, the suturing device is inserted through a puncture wound. The guiding tracks are rotated to drive the needles through adjacent tissue. At this point, the needles are driven into a catch mechanism of the device. As the device is removed, the suture is pulled through the wound.

SUMMARY OF THE INVENTION

A method and apparatus for implanting a prosthesis for repairing tissue are disclosed. In one aspect, the invention provides a tissue repair system, comprising: a prosthesis including a first end portion and a second end portion; the first end portion including an engaging portion; the second end portion including a receiving portion that is configured to cooperate with the engaging portion; a delivery device configured to implant the prosthesis; the delivery device including a first delivery needle and a second delivery needle that are configured to penetrate through to a distal portion of a tissue, the distal portion of the tissue being disposed farther from a surgeon than a proximal portion of the tissue; the first delivery needle being associated with the engaging portion and the second delivery needle being associated with the receiving portion; and where the first delivery needle and the second delivery needle are configured to fasten the engaging portion to the receiving portion on the distal portion of the tissue.

In another aspect, the receiving portion includes a hole.

In another aspect, the engaging portion includes a catching member.

In another aspect, the prosthesis is a suture.

In another aspect, the engaging portion includes a knot.

In another aspect, the receiving portion includes a loop to receive the knot.

In another aspect, the invention provides a tissue repair system, comprising: a prosthesis including an engaging portion and a receiving portion; a delivery device configured to implant the prosthesis; the delivery device comprising a first delivery needle that is configured to move inward and a second delivery needle that is configured to move inward; the first delivery needle being associated with the engaging portion and the second delivery needle being associated with the receiving portion; and where the first delivery needle and the second delivery needle may move inward in a manner that aligns the engaging portion with the receiving portion.

In another aspect, the first delivery needle is associated with a first end portion and wherein the second delivery needle is associated with an intermediate portion disposed adjacent to a second end portion of the second delivery needle.

In another aspect, the first end portion of the first delivery needle is configured to align with the intermediate portion of the second delivery needle.

In another aspect, the first delivery needle and the second delivery needle are associated with an actuator that may be used to move the first delivery needle and the second delivery needle.

In another aspect, the actuator may be associated with a tensioning member that may be used to apply a force to control the actuator.

In another aspect, the first delivery needle includes an open channel.

In another aspect, the delivery device includes a pushing member disposed within the open channel and wherein the pushing member is configured to facilitate delivery of the prosthesis.

In another aspect, the invention provides a method of implanting a prosthesis, comprising the steps of: delivering a first end portion and a second end portion of a prosthesis on a distal portion of a tissue, where the distal portion is disposed farther from a surgeon than a proximal portion of the tissue; delivering an intermediate portion of a prosthesis to the proximal portion of the tissue; and fastening the first end portion to the second end portion.

In another aspect, the step of delivering the first end portion and the second end portion of the prosthesis includes a step of associating a delivery device with the tissue.

In another aspect, a portion of the delivery device is disposed within a cannula.

In another aspect, the step of fastening the first end portion to the second end portion includes a step of moving a first delivery needle of the delivery device and a second delivery needle of the delivery device inward.

In another aspect, the step of moving the first delivery needle and the second delivery needle includes a step of pulling a tensioning member inward.

In another aspect, the step of fastening includes a step of applying a force to at least one pushing member that is configured to contact a portion of the prosthesis.

In another aspect, the step of fastening is followed by a step of removing the delivery device.

Other systems, methods, features and advantages of the invention will be, or will become apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1A:
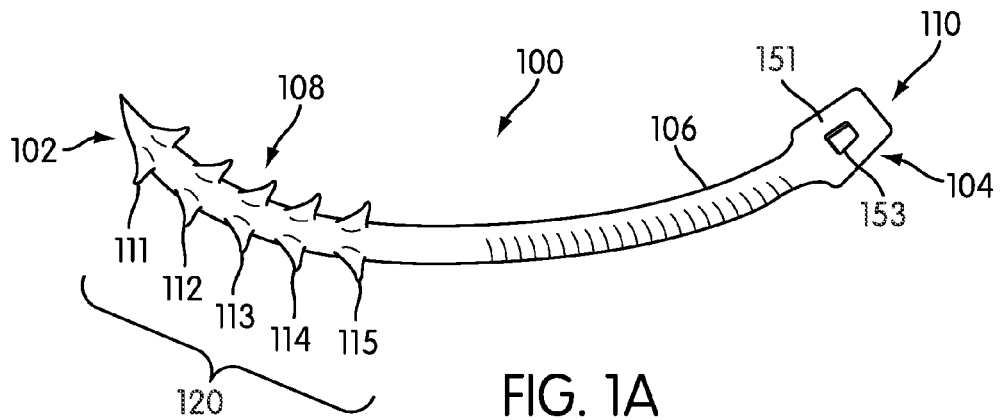
FIG. 1A is a plan view of an embodiment of a prosthesis.

FIG. 1A is a plan view of an embodiment of prosthesis 100. Generally, prosthesis 100 may be used for repairing or improving any flaw, imperfection, cut, incision, hole, or tear in various types of tissue throughout the human body or for retaining a first tissue in a desired position proximate a second tissue. The term "tissue" as used throughout this detailed description and in the claims refers to any collection of interconnected cells that perform a similar function within an organism. Examples of different types of biological tissue can include without limitation ligaments, tendons, facia, cartilage, bone, muscle tissue and nervous tissue.

Prosthesis 100 may comprise first end portion 102 and second end portion 104. In this embodiment, first end portion 102 is joined to second end portion 104 by intermediate portion 106. Generally, intermediate portion 106 may be configured with any length that allows prosthesis 100 to repair or improve an imperfection in tissue or retain it in a desired position. In some embodiments, intermediate portion 106 may provide a rigid connection between first end portion 102 and second end portion 104. In this preferred embodiment, however, intermediate portion 106 may be flexible and allow for relative motion of first end portion 102 with respect to second end portion 104.

Preferably, prosthesis 100 includes provisions for fastening first end portion 102 to second end portion 104. In this embodiment, first end portion 102 may include engaging portion 108. In particular, engaging portion 108 may be disposed on a length of first end portion 102. Similarly, second end portion 104 may include receiving portion 110. With this arrangement, prosthesis 100 may be fastened by inserting engaging portion 108 through receiving portion 110.

Engaging portion 108 may comprise a plurality of catching members. Generally, any type of catching or latching member known in the art can be used, such as uni-directional latching mechanisms. For example, a catching member can be a two-dimensional or three-dimensional protrusion configured to engage receiving portion 110 (FIGS. 1A and 1C). The protrusions can include any appropriate shape such as a knot or ball, a rounded protrusion, a flared protrusion, a triangular protrusion, etc.

In some embodiments, engaging portion 108 may comprise a single catching member. In other embodiments, engaging portion 108 may comprise more than one catching member. In the current embodiment of FIG. 1A, engaging portion 108 includes a series of five catching members that comprise catching member set 120. Catching member set 120 preferably includes first catching member 111, second catching member 112, third catching member 113, fourth catching member 114 and fifth catching member 115.

Generally, catching member set 120 of engaging portion 108 may be configured in any manner to engage receiving portion 110. In some cases, catching members from catching member set 120 may protrude with a rounded shape from first end portion 102. In other cases, the catching members of catching member set 120 may be constructed with a plurality of substantially triangular shapes projecting from first end portion 102. In the present embodiment of FIG. 1A, for example, first catching member 111 includes a pair of opposite triangular shapes protruding radially. In some cases, the remaining catching members of catching member set 120 may have substantially similar shapes to first catching member 111. Preferably, this configuration allows engaging portion 108 to be inserted through receiving portion 110 in a fastening direction and thereby prevents engaging portion 108 from slipping out of receiving portion 110 in an unfastening direction.

Generally, receiving portion 110 may include any provisions for receiving engaging portion 108. In some embodiments, receiving portion 110 may be tied into a lasso knot to accommodate engaging portion 108. In a preferred embodiment, receiving portion 110 may include ring 151 with hole 153 to accommodate engaging portion 108. With this arrangement, receiving portion 110 may cooperate with engaging portion 108. In particular, catching members of catching member set 120 may be inserted through hole 153 of receiving portion 110. As the catching members of catching member set 120 are caught within hole 153, first end portion 102 may be fastened to second end portion 104.

Although one particular embodiment of prosthesis 100 is illustrated in FIG. 1A, the size, shape, and other characteristics of first end portion 102, second end portion 104 and intermediate portion 106 of prosthesis 100 may be determined based on a number of factors, potentially including the size and shape of the imperfection; the condition and type of tissue that may be repaired or retained using prosthesis 100; and the type and amount of circumferential or other stress that is to be exerted by prosthesis 100 on the surrounding tissue during the implantation process.

Prosthesis 100 may be made from one or more materials suitable for a suture including, but not limited to, chromic catgut, polyglycolic acid (PGA), or polydioxanone (PDS). In some embodiments, some portions of prosthesis 100 may be made of a generally rigid material while other portions of prosthesis 100 may be made of a generally flexible material. In some cases, first end portion 102 and second end portion 104 may be made of a generally rigid material. Likewise, intermediate portion 106 may be made of a generally flexible material. For example, prosthesis 100 may be made of materials including, but not limited to, metal or plastic. Using a rigid material for first end portion 102 and second end portion 104 and a flexible material for intermediate portion 106 may facilitate the fastening of prosthesis 100. In other embodiments, first end portion 102, second end portion 104 and intermediate portion 106 could all be made of a substantially similar material.

In other embodiments, however, prosthesis 100 could be made of other materials. In some cases, for example, it may be preferable to make prosthesis 100 using a biocompatible material that is sufficiently rigid to hold a cut or incision closed in some types of tissue, yet sufficiently compliant so as to avoid further damaging the tissue should slight relative motion between the tissue and prosthesis 100 occur. Examples of suitable materials include nylon, prolene, dacron, ultra high molecular weight polyethylene (UHMWPE), and other suitable suture materials.

In still other embodiments, prosthesis 100 may be formed of a bioabsorbable polymer that is gradually absorbed by the body. Some examples of suitable bioabsorbable materials are: poly L-lactic acid (PLLA) and polyglycolic acid (PGA). Prosthesis 100 can also be formed of other possible materials, including without limitation polytetrafluorethylene (PTFE), polyaryletherketone (PAEK), polyetheretherketone (PEEK), polyoxymethylene (acetal), polycarbonate, polysulfone, silicone elastomers, commercially pure titanium, titanium alloys, CoCr alloys, nickel titanium (nitinol) alloys and implant grade stainless steels.

Preferably, an imperfection in tissue may be repaired by implanting and fastening a prosthesis at the site of the imperfection, or a tissue may be retained proximate another tissue by implanting and fastening a prosthesis while the tissues are in their desired positions. In prior designs, a prosthesis implanted to repair or retain tissue may be fastened on a proximal portion of the tissue. The terms "proximal portion" as used throughout this detailed description and in the claims refers to a portion of a tissue that is disposed closest to a surgeon during implantation. Likewise, the term "distal portion" as used throughout this detailed description and in the claims refers to a portion of tissue disposed furthest from a surgeon during implantation.

In some cases, the fastening of a prosthesis on a proximal side of tissue may cause irritation that interferes with healing. For example, sutures are typically closed on a proximal side of tissue leaving small knots that can irritate adjacent tissue. In a preferred embodiment, a prosthesis may be fastened on a distal side of tissue. Preferably, fastening a prosthesis on a distal side of tissue prevents irritation on a proximal side of tissue and enhances healing.

Figure 1B:
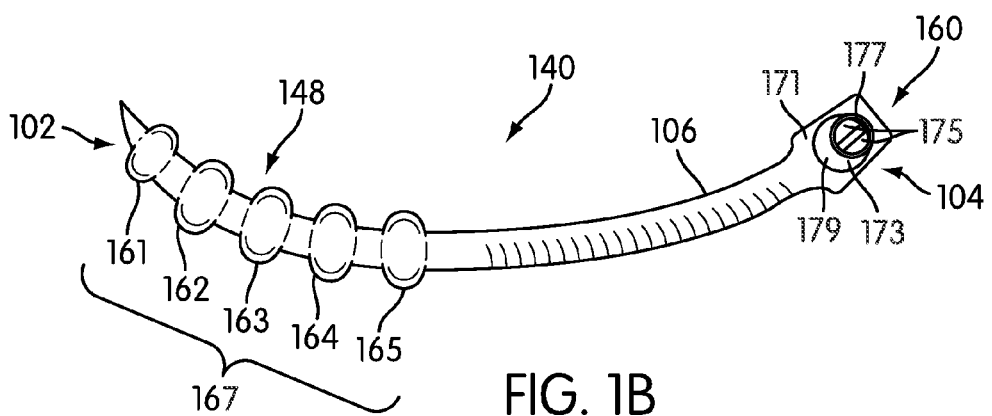
FIG. 1B is a plan view of another embodiment of a prosthesis.
Figure 1C:
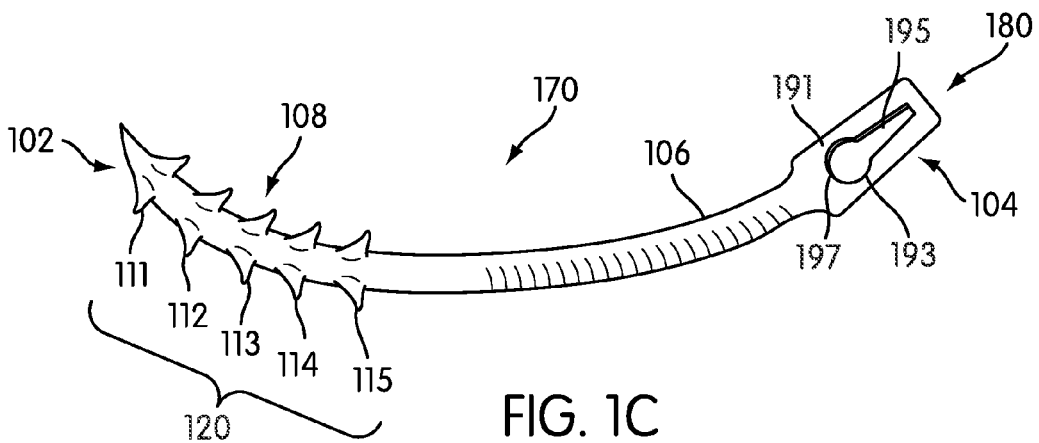
FIG. 1C is a plan view of an additional embodiment of a prosthesis.

FIG. 1B is a plan view of another embodiment of prosthesis 140, which generally includes the aspects and features of prosthesis 100 except as discussed hereafter. As shown, prosthesis 140 includes engaging portion 148 on a length of first end portion 102 and a receiving portion 160 at opposite second end portion 104. Engaging portion 148 can include a catching member set 167 having a series of rounded catching members in the form of knots or balls. The catching members can include first catching member 161, second catching member 162, third catching member 163, fourth catching member 164 and fifth catching member 165, which can be about the same size or have differing sizes. For instance, the catching members can increase in size from the first catching member 161 to the fifth catching member 165.

As also shown in FIG. 1B, receiving portion 160 can include end tab 171 having catch 173 in the form of a funnel-like entryway. For example, catch 173 can be a rectangular, cylindrical or conical gateway and can have walls 179 angled toward each other and one or more unidirectional latches 175 at an exit hole 177, which can lock catching members when inserted through exit hole 177. Walls 179 can form a channel to guide the catching members toward exit hole 177 and to inhibit bending of engaging portion 148 when the catching members are being pushed past latches 175 through exit hole 177.

Figure 10:
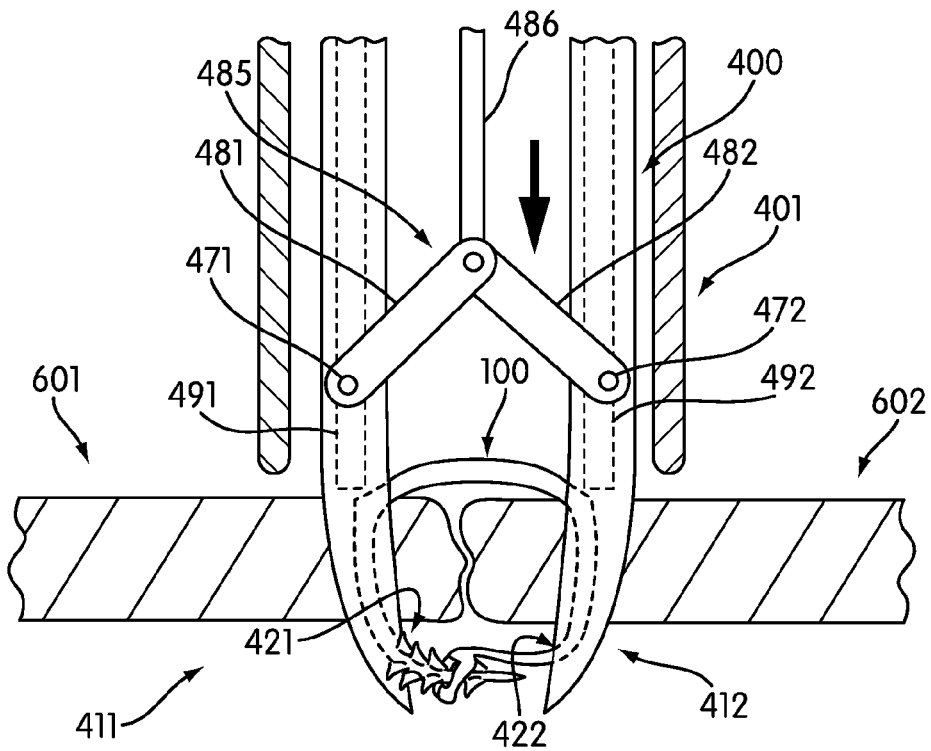
FIG. 10 is a cross sectional view of an embodiment of a delivery device releasing a prosthesis that is fastened and implanted into a first tissue and a second tissue.

FIG. 10 is a plan view of a further embodiment of prosthesis 170, which generally includes the aspects and features of prosthesis 100 except as discussed hereafter. As shown, prosthesis 170 includes receiving portion 180 at second end portion 104. Receiving portion 180 can include end tab 191 having slot 193 formed therein. Slot 193 can include a large entry opening 197 at a first end leading to a narrow retaining portion 195 at an opposite second end. Preferably, large entry opening 197 is larger than narrow retaining portion 195 and generally constricts as it leads toward narrow retaining portion 195.

In some cases, narrow retaining portion 195 can form a slot having a generally constant width. In the case shown in FIG. 10, narrow retaining portion 195 can be tapered along its length as it extends from large entry opening 197 toward its opposite end. As such, engaging portion 108 and catching members of catching member set 120 can easily enter and extend through hole 193 during installation. While prosthesis 170 is being fastened, it is typically placed under tension along its length and in some cases may stretch, and tissue it surrounds is compressed. When installation and fastening forces are withdrawn, tensile stresses along the length of prosthesis 170 are reduced and the compressed tissues expand, which encourages catching member set 120 inserted through large entry opening 193 to slide into narrow retaining portion 195. This can lock the catching members in the narrow retaining portion to form a secure connection.

Figure 2:
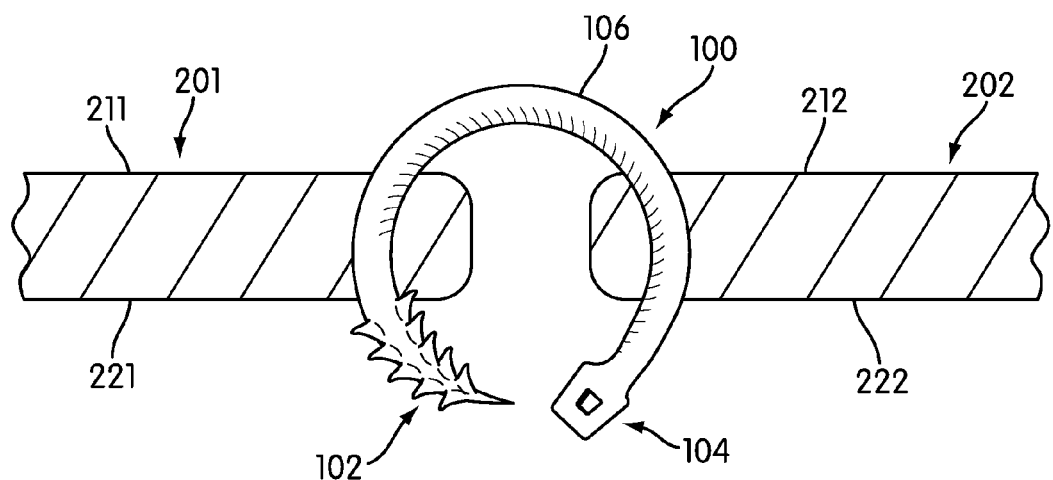
FIG. 2 is a cross sectional view of an embodiment of a fastening of a prosthesis to retain a first tissue proximate a second tissue.
Figure 3:
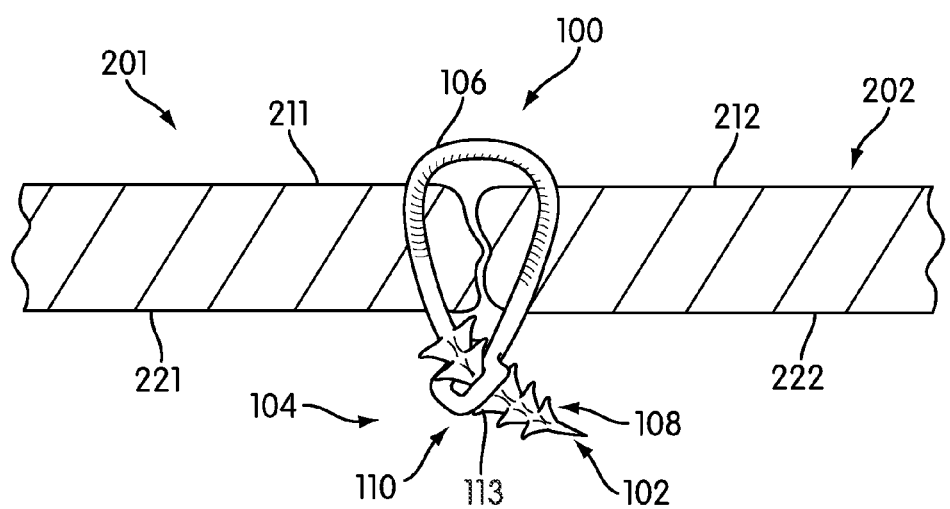
FIG. 3 is a cross sectional view of an embodiment of a prosthesis fastened to retain a first tissue proximate a second tissue.

FIGS. 2-3 illustrate a cross sectional view of an exemplary embodiment of a method of fastening prosthesis 100 to reattach first tissue 201 to second tissue 202, or to retain first tissue 201 in a desired configuration proximate second tissue 202. In this embodiment, first tissue 201 and second tissue 202 may be portions of a single tissue that has ruptured. The current embodiment is intended to be exemplary and could be applied to various different situations in which one tissue must be reattached or retained proximate to a second tissue.

In this embodiment, first end portion 102 is inserted through first tissue 201. In particular, first end portion 102 may be inserted through first proximal side 211 of first tissue 201 and emerge on first distal side 221 of first tissue 201. Additionally, second end portion 104 may be inserted through second tissue 202. In a similar manner to first end portion 102, second end portion 104 may pierce second proximal side 212 of tissue 202. Following this insertion, second end portion 104 may pass through second tissue 202 to emerge on second distal side 222 of second tissue 202. With this arrangement, first end portion 102 and second end portion 104 may be disposed on first distal side 221 and second distal side 222, respectively.

Referring to FIG. 2, the configuration of first end portion 102 and second end portion 104 on first distal side 221 and second distal side 222, respectively, disposes intermediate portion 106 on first proximal side 211 and second proximal side 212. Preferably, intermediate portion 106 provides a substantially smooth surface to first proximal side 211 and second proximal side 212 to help reduce irritation.

Referring to FIG. 3, first tissue 201 and second tissue 202 may be pulled closer together through the fastening of first end portion 102 and second end portion 104. In order to fasten prosthesis 100, engaging portion 108 of first end portion 102 may be threaded through receiving portion 110. Due to the shape of engaging portion 108, receiving portion 110 may accommodate the insertion of engaging portion 108 but prevent engaging portion 108 from slipping out of receiving portion 110. In some cases, a desired configuration of prosthesis 100 may be associated with a desired tautness of prosthesis 100. In other cases, a desired configuration of prosthesis may be associated with a position of first tissue 201 and second tissue 202. In this embodiment, receiving portion 110 catches on third catching member 113 of engaging portion 108 to fasten prosthesis 100 so that first tissue 201 and second tissue 202 may be held together.

With this arrangement, prosthesis 100 may be fastened on first distal side 221 and second distal side 222 to hold first tissue 201 and second tissue 202 together. Furthermore, this method of fastening allows prosthesis 100 to be implanted with intermediate portion 106 disposed on first proximal side 211 and second proximal side 212. Preferably, intermediate portion 106 provides a smooth surface on first proximal side 211 and second side 212 to prevent irritation and improve healing.

Figure 4:
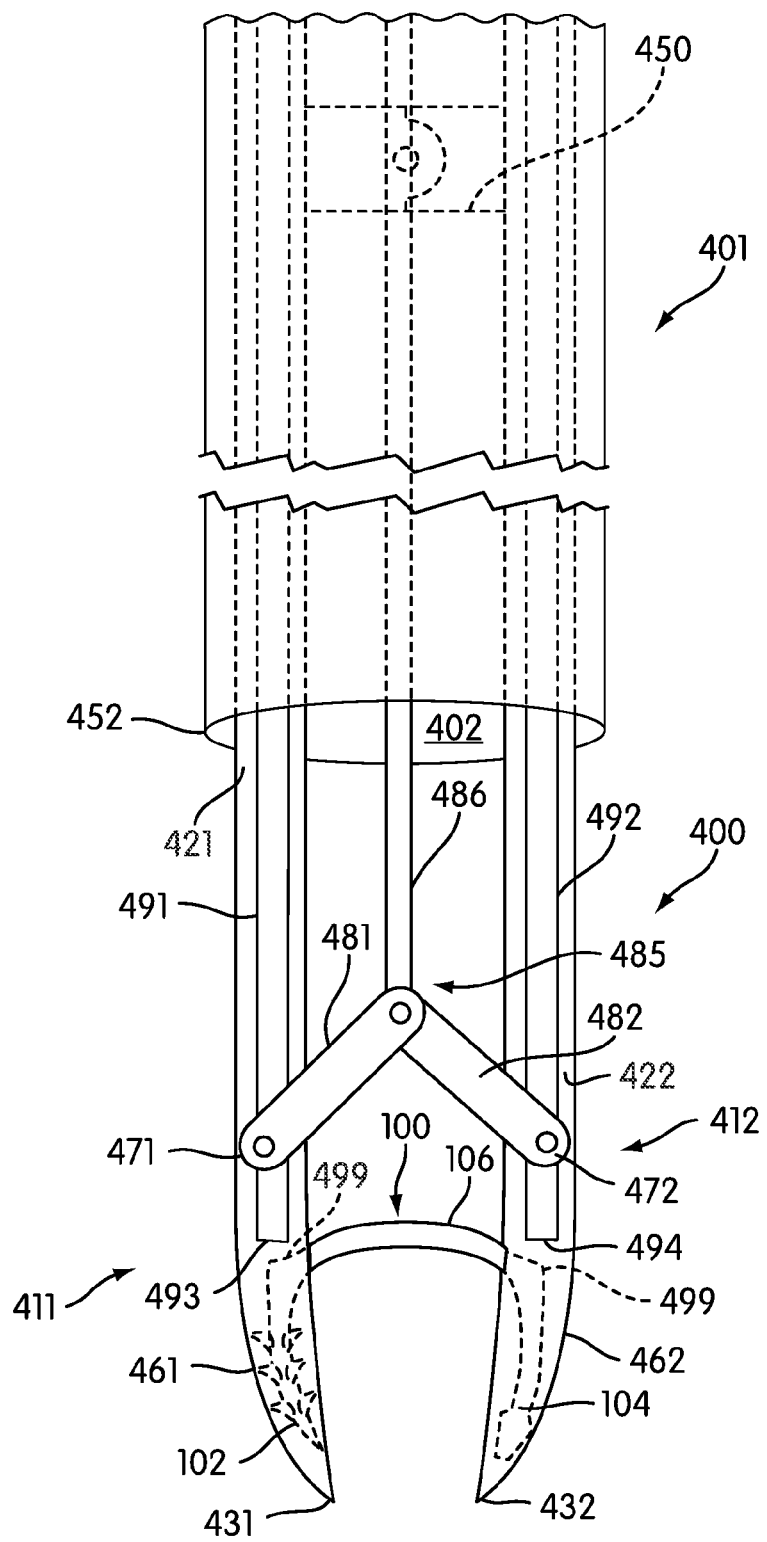
FIG. 4 is a plan view of an embodiment of a delivery device configured to implant and fasten a prosthesis.
Figure 5:
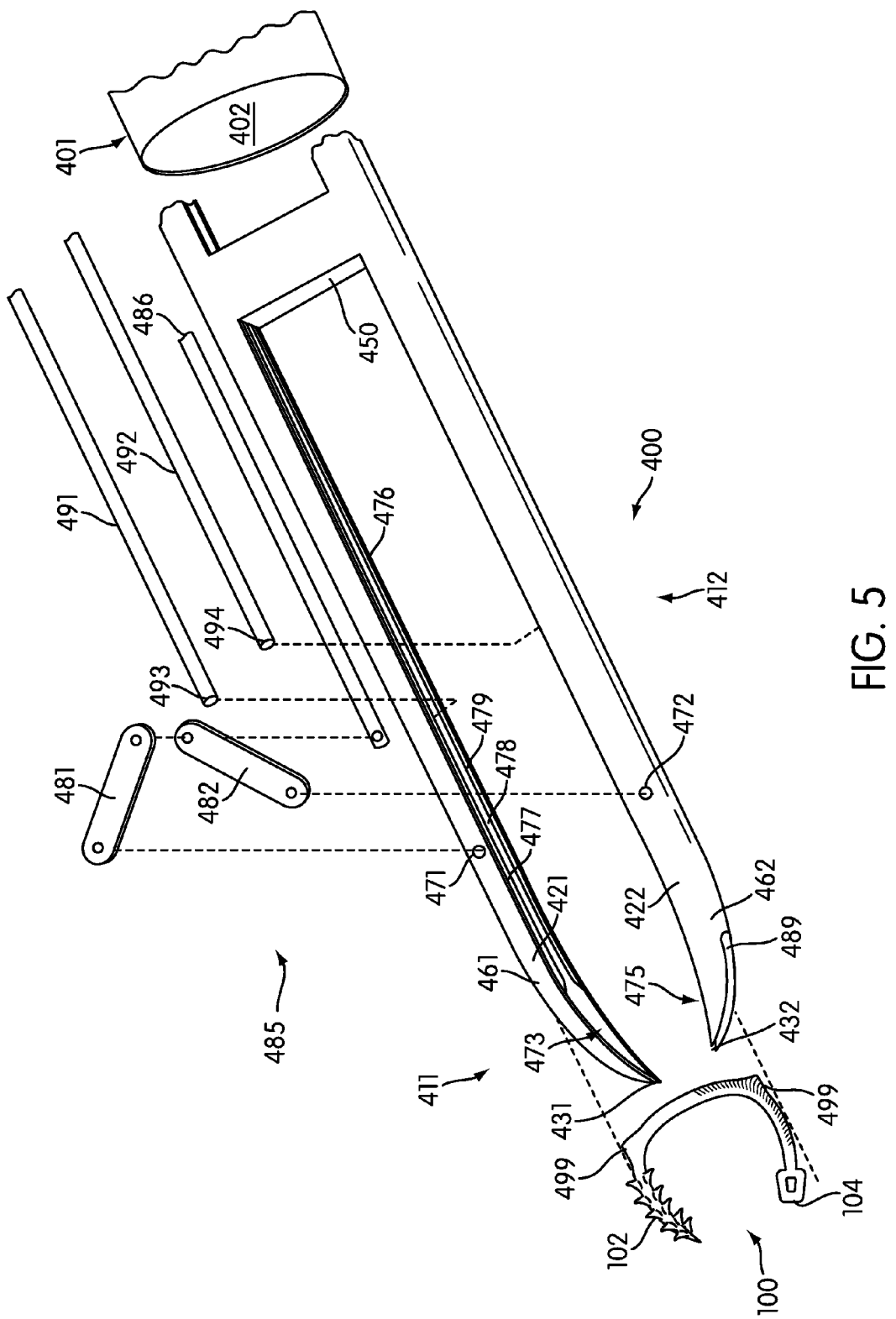
FIG. 5 is an exploded isometric view of an embodiment of a delivery device configured to implant and fasten a prosthesis.

Preferably, prosthesis 100 may be associated with a delivery device that can implant a prosthesis 100 at a proximal side of one or more tissues and fasten it on a distal side. FIGS. 4-5 illustrate a preferred embodiment of delivery device 400. FIG. 4 is a plan view of a preferred embodiment of delivery device 400 and FIG. 5 is an exploded isometric view of a preferred embodiment of delivery device 400.

Referring to FIG. 4, delivery device 400 may be associated with delivery cannula 401. Generally, delivery cannula 401 may be any type of tube that is configured to insert into the body and may include one or more channels for delivering one or more devices. In this preferred embodiment, delivery cannula 401 includes delivery lumen 402 for accommodating delivery device 400. Delivery cannula 401 and delivery lumen 402 preferably both include distal end portion 452 that is configured to be placed near a treatment area of one or more tissues.

Delivery device 400 preferably comprises several components configured to implant and fasten prosthesis 400 into some kind of tissue in need of repair. In this embodiment, delivery device 400 comprises first delivery needle 411 and second delivery needle 412. In some cases, first delivery needle 411 and second delivery needle 412 may be disposed within all or a portion of delivery lumen 402.

In some embodiments, first delivery needle 411 and second delivery needle 412 are generally hollow. In a preferred embodiment, first delivery needle 411 and second delivery needle 412 may be partially opened as seen in FIG. 5. In particular, first delivery needle 411 may include first open channel 421. Also, second delivery needle 412 may include second open channel 422. First and second delivery needles 411 and 412 can have various shapes including square, round, oval or rectangular. In a preferred embodiment, first open channel 421 and second open channel 422 are generally round or oval shaped and may have C-shaped cross sections. With this configuration, first open channel 421 and second open channel 422 are configured to receive prosthesis 100 in a manner that allows prosthesis 100 to slide between first delivery needle 411 and second delivery needle 412 while allowing first end portion 102 and second end portion 104 of prosthesis 100 to be partially restrained within first delivery needle 411 and second delivery needle 412, respectively. As shown in FIG. 4, first and second delivery needles 411 and 412 can be curved at the end portions. In another embodiment, first and second delivery needles 411 and 412 can be straight throughout including at the end portions.

Generally, first open channel 421 may extend throughout first intermediate portion 461 of first delivery needle 411. Likewise, second open channel 422 may extend throughout second intermediate portion 462 of second delivery needle 412. In other embodiments, first open channel 421 and second open channel 422 may extend through only parts of first intermediate portion 461 and second intermediate portion 462, respectively.

First delivery needle 411 and second delivery needle 412 can be piercing needles and can also include tapered ends configured to contact and navigate past tissue, and in some cases penetrate through tissue. In this embodiment, first delivery needle 411 and second delivery needle 412 may include first needle end 431 and second needle end 432, respectively. In a preferred embodiment, first needle end 431 and second needle end 432 are tapered to provide sharpened tips. In some cases, this tapered configuration of first needle end 431 and second needle end 432 may provide for wider openings of first open channel 421 and second open channel 422.

In some embodiments, first delivery needle 411 and second delivery needle 412 may be attached via an optional connector 450. In some cases, connector 450 may be attached to first delivery needle 411 and second delivery needle 412. This arrangement preferably provides structural stability and a rigid connection for first delivery needle 411 and second delivery needle 412. Furthermore, this arrangement of connector 450 may provide a pivoting point for first delivery needle 411 and second delivery needle 412.

Generally, connector 450 can be any type of structure that connects first delivery needle 411 and second delivery needle 412. In some embodiments, connector 450 can be a solid connector (see e.g., FIG. 5). In the embodiment shown in FIG. 4, connector 450 may be a hinged connector. It can also be a solid connector that flexes to act as a living hinge during use. With this arrangement, first delivery needle 411 and second delivery needle 412 may be disconnected in some situations.

Connector 450 may be associated with any portion of first delivery needle 411 and second delivery needle 412. In some cases, connector 450 may be disposed near first needle end 431 and second needle end 432. Preferably, connector 450 may be disposed far away from first needle end 431 and second needle end 432.

Preferably, first delivery needle 411 and second delivery needle 412 may be configured to align first end portion 102 and second end portion 104 of prosthesis 100 in order to fasten prosthesis 100. In some embodiments, first delivery needle 411 and second delivery needle 412 may include first pivoting portion 471 and second pivoting portion 472, respectively. First pivoting portion 471 and second pivoting portion 472 may be configured to receive an actuating force that causes first delivery needle 411 and second delivery needle 412, respectively, to move towards one another to fasten first end portion 102 and second end portion 104 of prosthesis 100.

In some embodiments, first pivoting portion 471 and second pivoting portion 472 may receive an actuating force from actuator 485. In some cases, actuator 485 may include first portion 481 and second portion 482. In this embodiment, first pivoting portion 471 may be connected to first portion 481 of actuator 485. Likewise, second pivoting portion 472 may be connected to second portion 482 of actuator 485. Furthermore, first portion 481 and second portion 482 of actuator 485 may attach together at tensioning member 486. Preferably, tensioning member 486 may be manipulated by a surgeon to move actuator 485 and first pivoting portion 471 and second pivoting portion 472. With this configuration, actuator 485 may be used to control the motion of first delivery needle 411 and second delivery needle 412.

Generally, tensioning member 486 could be any device for applying tension to actuator 485. In some embodiments, tensioning member 486 could be a rod made of any substantially flexible material. In other embodiments, tensioning member 486 could be a cable of some kind. In yet other embodiments, tensioning member 486 can be substantially rigid and formed as a solid bar or tube made of a relatively stiff material. Tensioning member 486 can be a rod made of rigid material such as plastic or metal. In a preferred embodiment, tensioning member 486 is a stainless steel rod. With this arrangement, tensioning member 486 can easily be inserted through cannula 401 while providing enough stiffness to apply tension to actuator 485.

In this embodiment, actuator 485 may exert a first force on first pivoting portion 471 and second pivoting portion 472, when tensioning member 486 is pulled upward. In some cases, first portion 481 and second portion 482 may pull first delivery needle 411 and second delivery needle 412 inward to a closed position, when tensioning member 486 is pulled upward. In the closed position, first delivery needle 411 and second delivery needle 412 may be aligned to fasten first end portion 102 and second end portion 104. (See e.g., FIGS. 8 and 9).

In some embodiments, actuator 485 may exert a second force on first pivoting portion 471 and second pivoting portion 472, when tensioning member 486 is pushed downward. (See e.g., FIG. 4). In particular, first portion 481 and second portion 482 of actuator 485 may push first delivery needle 411 and second delivery needle 412 outward to an open position when tensioning member 486 is pushed downward. In the open position, first delivery needle 411 and second delivery needle 412 may be disposed some distance away from each other. This will be discussed in further detail later in this detailed description.

Preferably, delivery device 400 includes provisions for applying a force for implantation and fastening of prosthesis 100. In some embodiments, delivery device 400 may be associated with first pushing member 491 and second pushing member 492. First pushing member 491 and second pushing member 492 are preferably configured to insert into first open channel 421 and second open channel 422, respectively. In addition, first pushing member 491 and second pushing member 492 may extend to a proximal end of delivery device 400 that is not visible in these Figures.

In a preferred embodiment, first pushing member 491 and second pushing member 492 are substantially rigid and configured to transfer a force applied at a proximal end of delivery device 400 to first distal end portion 493 and second distal end portion 494, respectively. With this arrangement, first pushing member 491 and second pushing member 492 may be used to transfer a force to prosthesis 100 that may assist in the fastening and implantation of prosthesis 100. In particular, first pushing member 491 may transfer a force to first end portion 102 and second pushing member 492 may transfer a force to second end portion 104.

In some embodiments, first end portion 102 and second end portion 104 may include provisions for receiving first pushing member 491 and second pushing member 492. In this preferred embodiment, first end portion 102 and second end portion 104 may include flattened portions 499 that are shaped to receive first pushing member 491 and second pushing member 492. This preferred arrangement may facilitate the implantation of first end portion 102 and second end portion 104 by first pushing member 491 and second pushing member 492, respectively.

In some embodiments, first pushing member 491 and second pushing member 492 may be rigidly connected using one or more connecting members. This arrangement may help apply forces to first end portion 102 and second end portion 104 simultaneously. In other embodiments, first pushing member 491 and second pushing member 492 may not be rigidly attached and may be capable of relative motion with respect to one another. In these embodiments, a force may be applied to first pushing member 491 and second pushing member 492 separately to fasten first end portion 102 and second end portion 104.

Generally, various different types of materials may be used for constructing delivery device 400. Preferably, first delivery needle 411 and second delivery needle 412 may be made of rigid materials. In some cases, rigid plastics may be used. In other cases, materials may be used that include some type of metal. In a preferred configuration, the delivery needles are made of stainless steel.

Referring to FIGS. 4-5, assembly of delivery device 400 may proceed by connecting first portion 481, second portion 482, and tensioning member 486 of actuator 485. First portion 481 may be attached to first pivoting portion 471. Similarly, second portion 482 may be connected to second pivoting portion 472.

Following the assembly of actuator 485, prosthesis 100 may be loaded into first delivery needle 411 and second delivery needle 412 such that prosthesis ends 102 and 104 are disposed within first and second open channels 421 and 422 respectively and intermediate portion 106 bridges between the needles. As shown in FIG. 5, first and second delivery needles 411 and 412 can each include a pair of opposing guides 477 and 479 along their inner portions 476 spaced apart by a longitudinal gap 478. This arrangement of guides along the inner portions of the needles can form opposing tracks that aid retention of the prosthesis ends within the needle open channels while allowing the intermediate portions to bridge between the needles through gaps 478. Longitudinal gap 478 can extend along an intermediate portion of the needles and then open up proximate first and second needle ends 431 and 432 to form prosthesis exits 473 and 475.

The prosthesis exits can allow prosthesis ends 102 and 104 to exit open channels 421 and 422 at needle ends 431 and 432.

Figure 12:
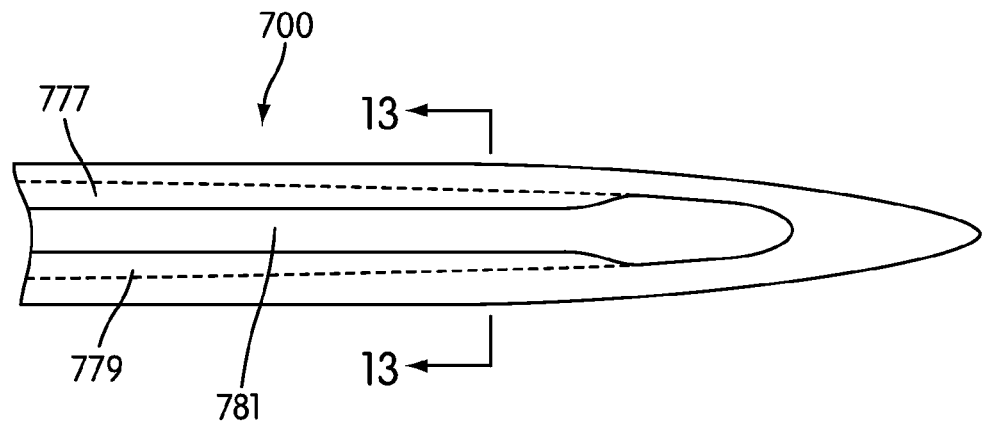
FIG. 12 is a plan view of an embodiment of a tip region of a needle for a delivery device configured to implant and fasten a prosthesis.
Figure 13:
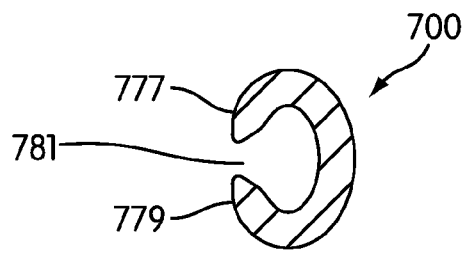
FIG. 13 is a cross-sectional view of the needle of FIG. 12 taken along line 13-13 in FIG. 12.

In other embodiments, the needles could be rounded needles, such as needle 700 shown in FIGS. 12 and 13 having rounded guides 777 and 779 spaced apart by gap 781. Rounded needles can be beneficial for reasons that can vary depending on the use and type of tissues involved, such as improved navigation past tissue or better penetration through it with less potential for tissue damage compared with needles having other cross-sectional shapes.

Returning to FIGS. 4 and 5 regarding assembly of delivery device 400, first end portion 102 of prosthesis 100 may be inserted into first open channel 421 of first delivery needle 411. In some cases, first end portion 102 and second end portion 104 may be loaded within first open channel 421 and second open channel 422 respectively proximate to first needle end 431. In other cases, the prosthesis end portions may be loaded at first intermediate portion 461 or at another location, such as at a control end of the delivery device. Furthermore, intermediate portion 106 of prosthesis 100 may be disposed between first delivery needle 411 and second delivery needle 412.

Following the loading of prosthesis 100, first pushing member 491 and second pushing member 492 may be inserted into first open channel 421 and second open channel 422, respectively. At this point, delivery device 400, including first delivery needle 411 and second delivery needle 412 as well as prosthesis 100 may be inserted into delivery lumen 402.

It should be understood that the order of assembling the components of delivery device 400 is intended to be exemplary. In other embodiments, the order of assembly may vary. Additionally, it should be understood that delivery device 400 may be associated with delivery cannula 401 at various times. In some cases, delivery device 400 may be inserted into delivery lumen 402 of delivery cannula 401 prior to moving delivery cannula 401 into position near the tissue to be treated. In other cases, delivery device 400 may be inserted into delivery lumen 402 after moving delivery cannula 401 into position near the tissue to be treated.

FIGS. 6-11 illustrate a preferred embodiment of a method of implanting prosthesis 100 using delivery device 400 in order to reattach first tissue 601 to second tissue 602 or to retain the tissues proximate each other, such as for moving the tissues close to each other or for closing a gap between tissues and using prosthesis 100 to retain them in the desired configuration. The current embodiment is intended to be generic and could be applied to various different situations in which one tissue must be reattached or retained proximate to a second tissue.

It should be understood that the following embodiment is not intended to be limiting and other uses for prosthesis 100 and delivery device 400 will be apparent to anyone skilled in the art. As previously discussed, delivery device 400 may be used with any type of tissue that requires repair and that is configured to receive prosthesis 100. Furthermore, the following embodiment does not include steps for loading prosthesis 100 within delivery device 400, which have already been discussed in the previous embodiments.

Figure 6:
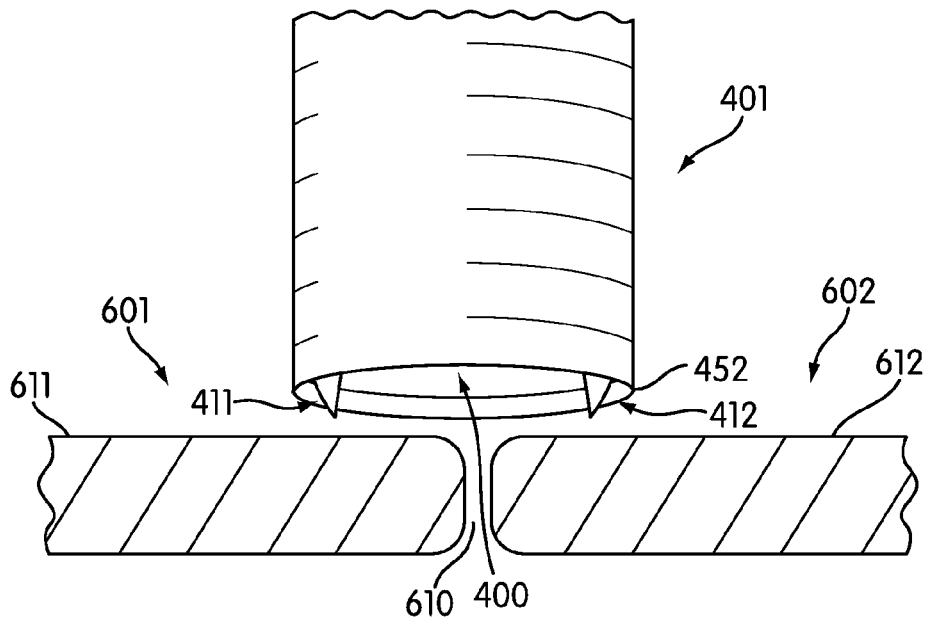
FIG. 6 is a cross sectional view of an embodiment of a delivery device with delivery needles retracted within a delivery cannula.

Referring to FIG. 6, delivery cannula 401 may be disposed in a position that allows prosthesis 100 to repair first tissue 601 and second tissue 602 or to retain them in a desired configuration proximate each other. In this embodiment, delivery cannula 401 is disposed above first proximal side 611 of first tissue 601 and second proximal side 612 of second tissue 602 to repair treatment area 610. The term "treatment area" as used through this detailed description and in the claims refers to the region of a tissue that may be repaired using a prosthesis of some kind.

Preferably, at this point, prosthesis 100 is loaded within delivery device 400. In some cases, first delivery needle 411 and second delivery needle 412 may be disposed just within distal end portion 452. In addition, first delivery needle 411 and second delivery needle 412 may be configured in an open position.

Figure 7:
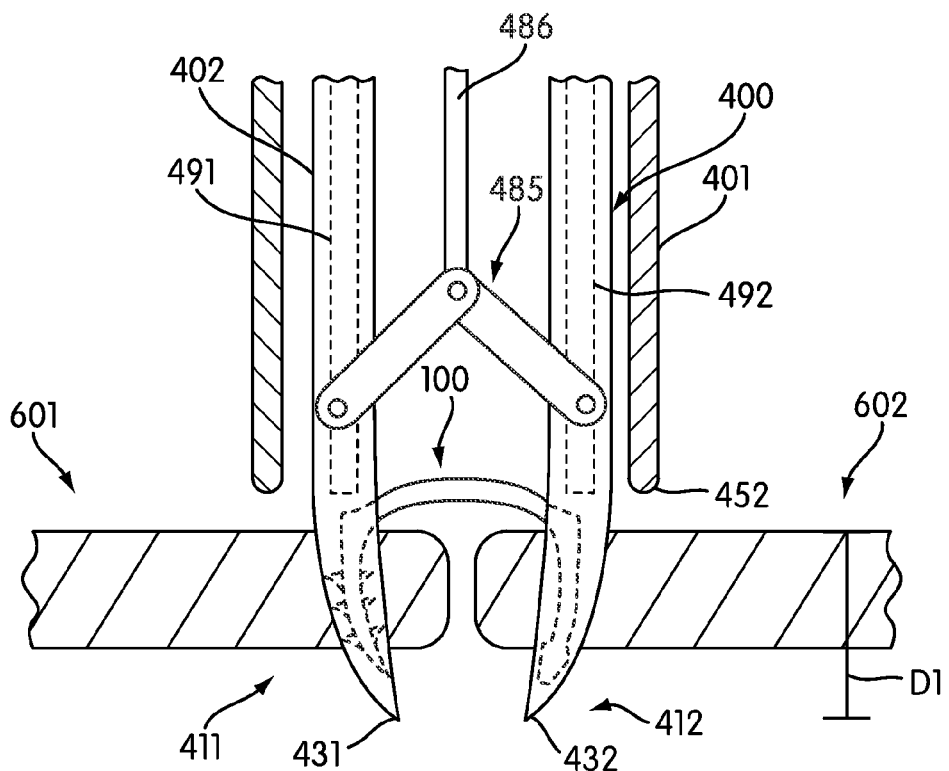
FIG. 7 is a cross sectional view of an embodiment of a prosthesis with delivery needles penetrating through a first tissue and a second tissue.

Referring to FIG. 7, first delivery needle 411 and second delivery needle 412 may be displaced from distal end portion 452 of delivery lumen 402. This configuration allows first needle end 431 and second needle end 432 to penetrate into first tissue 601 and second tissue 602, respectively. Generally, first needle end 431 and second needle end 432 may penetrate by any desired amount into first tissue 601 and second tissue 602, respectively. In some embodiments, first needle end 431 and second needle end 432 may penetrate into first tissue 601 and second tissue 602 distance D1 below first proximal side 611 and second proximal side 612, respectively. In some cases, the value of distance D1 may vary in the range between 1 millimeter and 2 centimeters. In certain embodiments, the value of distance D1 is approximately 1 centimeter. With this arrangement, first needle end 431 and second needle end 432 may help implant prosthesis 100 into first tissue 601 and second tissue 602.

Figure 8:
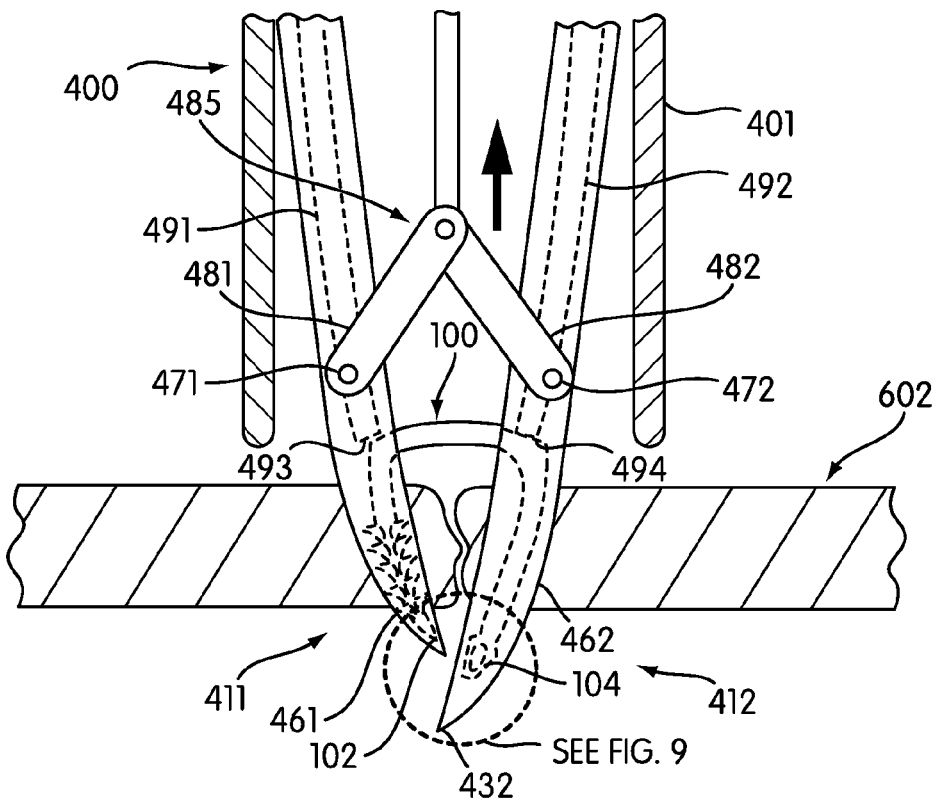
FIG. 8 is a cross sectional view of an embodiment of delivery needles of a delivery device rotating to align and insert an engaging portion of a prosthesis through a receiving portion of the prosthesis in order to fasten the prosthesis.

Following penetration into first tissue 601 and second tissue 602 by a desired amount, in a preferred embodiment a surgeon may pull tensioning member 486 away from delivery device 400 to apply a force to actuator 485 as seen in FIG. 8. Generally, any manner known in the art may assist a surgeon in pulling tensioning member 486. In some embodiments, tensioning member 486 may be attached to another mechanical apparatus, such as levers, that allows a surgeon to apply a compressive force that pulls tensioning member 486 away from delivery device 400. In other embodiments, a surgeon may grasp tensioning member 486 and apply a manual force.

As tensioning member 486 is pulled, actuator 485 is forced to contract. In particular, first portion 481 of actuator 485 and second portion 482 of actuator 485 may contract towards one another. This configuration conveys a force to first pivoting portion 471 of first delivery needle 411 and second pivoting portion 472 of second delivery needle 412. Preferably, this force causes first delivery needle 411 and second delivery needle 412 to move towards one another into a closed position in order to align and fasten prosthesis 100.

Generally, any portions of first delivery needle 411 and second delivery needle 412 may be aligned to fasten prosthesis 100. In some embodiments, first needle end 431 and second needle end 432 may be aligned in order to fasten prosthesis 100. In some cases, first needle end 431 may contact second needle end 432 to fasten prosthesis 100. In other cases, first needle end 431 may be slightly spaced apart from second needle end 432 in order to fasten prosthesis 100. In a preferred embodiment, first needle end 431 may align with second intermediate portion 462 in order to fasten prosthesis 100.

As shown in FIG. 8, after first delivery needle 411 and second delivery needle 412 are aligned to fasten prosthesis 100, a force may be conveyed by first distal end portion 493 of first pushing member 491 to push first end portion 102 to intersect second end portion 104 of prosthesis 100. In some embodiments, second distal end portion 494 of second pushing member 492 may also convey a force to assist second end portion 104 in fastening to first end portion 102. Using this configuration, prosthesis 100 may be fastened.

Figure 9:
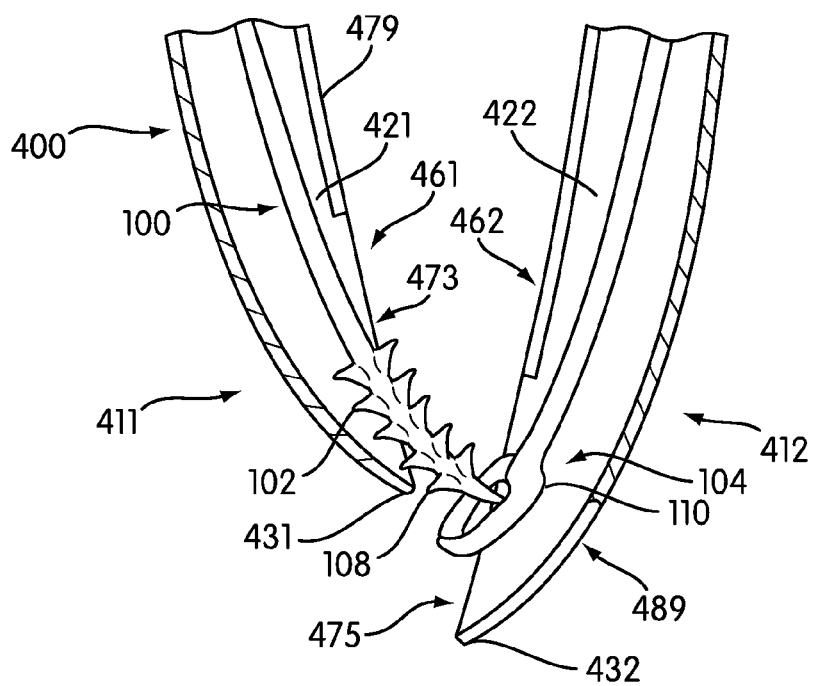
FIG. 9 is an enlarged cross sectional view of an embodiment of delivery needles aligned to insert an engaging portion of a prosthesis through a receiving portion of the prosthesis.

Referring to FIG. 9, an enlarged portion of FIG. 8, first needle end 431 is aligned with second intermediate portion 462. With this proximity of first needle end 431 and second intermediate portion 462, engaging portion 108 may be pushed outward from first open channel 421 by first pushing member 491 as previously discussed in reference to FIG. 8. In a similar manner, receiving portion 110 may be pushed outward from second open channel 422 by second pushing member 492 as seen in FIG. 8. Preferably, this allows engaging portion 108 to be inserted through receiving portion 110. As engaging portion 108 is inserted through receiving portion 110, engaging portion 108 will catch on receiving portion 110 as previously discussed in reference to FIGS. 2-3. With this arrangement, prosthesis 100 may be fastened by delivery device 400.

Figure 14:
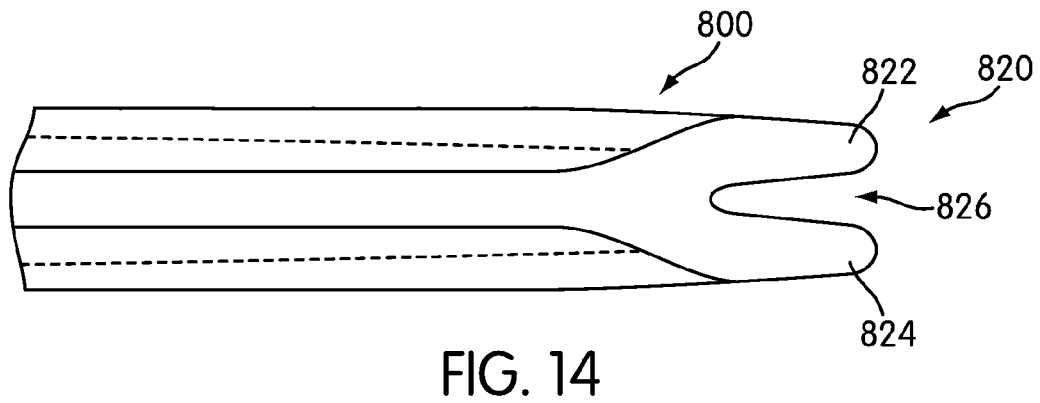
FIG. 14 is a plan view of a further embodiment of a tip region of a needle for a delivery device configured to implant and fasten a prosthesis.

Referring to FIGS. 5 and 9, second delivery needle 412 may include opening 489. Preferably, opening 489 may be configured to receive the tip of engaging portion 108 to prevent second delivery needle 412 from interfering with the fastening of prosthesis 100. In other words, as engaging portion 108 is inserted through receiving portion 110, the tip of engaging portion 108 may also extend through opening 489. With this arrangement, engaging portion 108 is not prevented from inserting farther through receiving portion 110 by a rear wall of second open channel 422. In other embodiments, the shape of second open channel 422 could be modified to help facilitate the fastening or prosthesis 100. Further, opening 489 can have various shapes, such as an open slot, and it could have a V-shaped or U-shaped notch at the tip of second delivery needle 412. As an example, FIG. 14 shows an embodiment of a needle 800 having a pair of prongs 822 and 824 at needle end 820 forming open U-shaped orifice 826 therebetween. Prongs 822 and 824 can form sharp tips for piercing tissue during insertion of the delivery device. In other cases, prongs 822 and 824 can form dull tips for navigating past or within tissue during insertion while avoiding unnecessary cutting.

In order to complete the implantation of prosthesis 100, delivery device 400 must fully release prosthesis 100. Referring to FIG. 10, tensioning member 486 may be pushed downward and actuator 485 may apply an outward force to first pivoting portion 471 and second pivoting portion 472. Preferably, this causes first delivery needle 411 and second delivery needle 412 to separate. In particular, first delivery needle 411 and second delivery needle 412 may be disposed in an open position. In another embodiment, during removal of delivery device 400, forces can be removed that previously biased first delivery needle 411 and second delivery needle 412 for insertion of the prosthesis. In one configuration, actuator 485 can be disengaged from one or both of the delivery needles 411 and 412. In another configuration, actuator 485 can be placed in a neutral force position to allow the delivery needles 411 and 412 movement flexibility during removal.

As first delivery needle 411 and second delivery needle 412 open outward, prosthesis 100 may be released. In particular, the fastening of prosthesis 100 may provide tension so that prosthesis 100 is ejected from first open channel 421 and second open channel 422 as first delivery needle 411 and second delivery needle 412 open outward. In some cases, first pushing member 491 and second pushing member 492 may assist in pushing prosthesis 100 from first open channel 421 and second open channel 422. With this configuration, prosthesis 100 may be expelled from delivery device 400 and implanted within first tissue 601 and second tissue 602.

Figure 11:
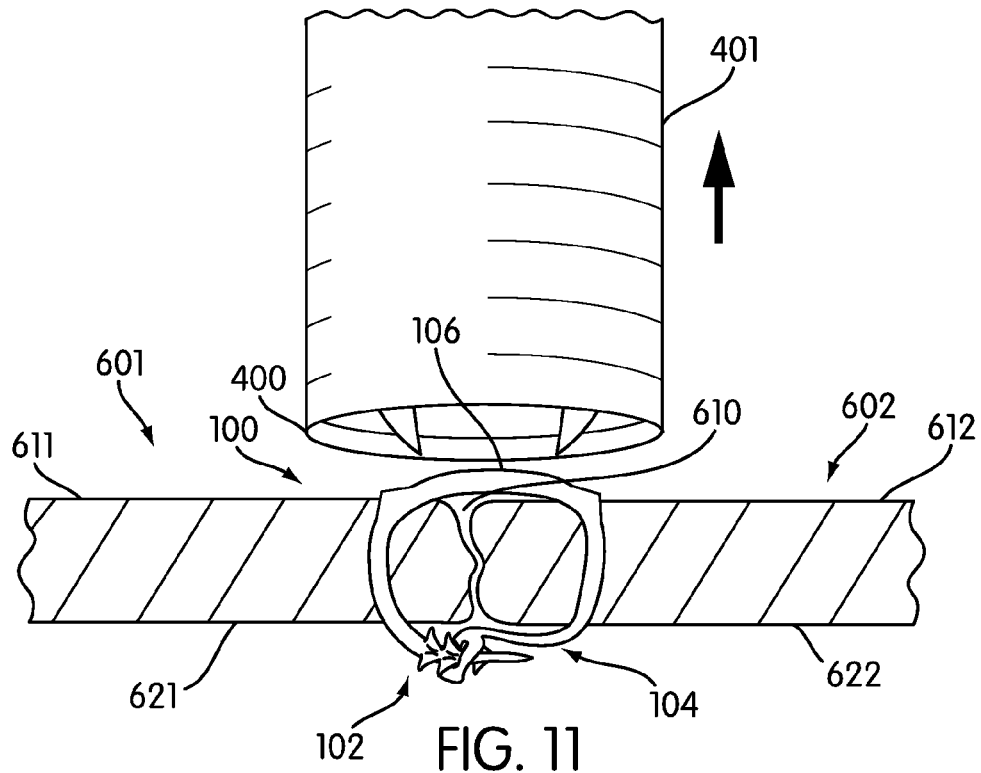
FIG. 11 is a cross sectional view of an embodiment of a prosthesis fully implanted into a first tissue and a second tissue

Referring to FIG. 11, following the implantation of prosthesis 100, delivery device 400 may be withdrawn into delivery cannula 401 and removed from treatment area 610. As seen in this Figure, the implantation of prosthesis 100 preferably attaches first tissue 601 to second tissue 602 or retains first tissue 601 in a desired configuration proximate second tissue 602. In addition, prosthesis 100 is implanted to provide minimal irritation to first proximal side 611 and second proximal side 612. In particular, first end portion 102 is fastened to second end portion 104 on first distal side 621 and second distal side 622. Furthermore, this fastening allows intermediate portion 106 to be disposed on first proximal side 611 and second proximal side 612. With this arrangement, intermediate portion 106 may apply a smooth surface to first proximal side 611 and second proximal side 612 to help facilitate healing of treatment area 610.

In some embodiments, a delivery device for a prosthesis may be operated without the use of a delivery cannula. For example, in some cases a surgeon may repair a portion of tissue that is disposed close to the surface of the skin, such as a bone or tendon in a foot or a hand. In this case, the delivery device, including first delivery needle and second delivery needle, first pushing member and second pushing member, actuator mechanism and a prosthesis, may be directly associated with the tissue without the use of a delivery cannula. In particular, the delivery needles may be located at the treatment area and the pushing members may be used to fasten the prosthesis on a distal side of the tissue.

For clarity, the previous embodiments illustrated in FIGS. 6-11 only show the use of a single prosthesis to repair tissue. It should be understood that in other embodiments, any number of prostheses could be applied in conjunction to repair one or more tissues. For example, in some cases, two prostheses could be used to repair tissue. In other cases, more than two prostheses could be used to repair tissue. Additionally, any shapes and/or orientations of one or more prostheses may be used in other embodiments. For example, in some cases an X-shaped configuration of two prostheses could be used. In other embodiments, various other types of geometric shapes or patterns may be formed using multiple prostheses. Using multiple prostheses in various shapes and patterns may allow a surgeon to obtain the desired tension and attachment configuration for the prostheses to promote healing of the damaged tissue.

Figure 15:
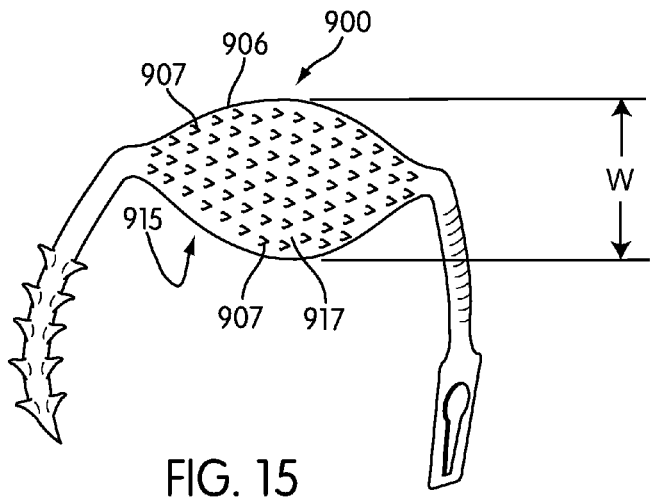
FIG. 15 is perspective view of an additional embodiment of a prosthesis.
Figure 16:
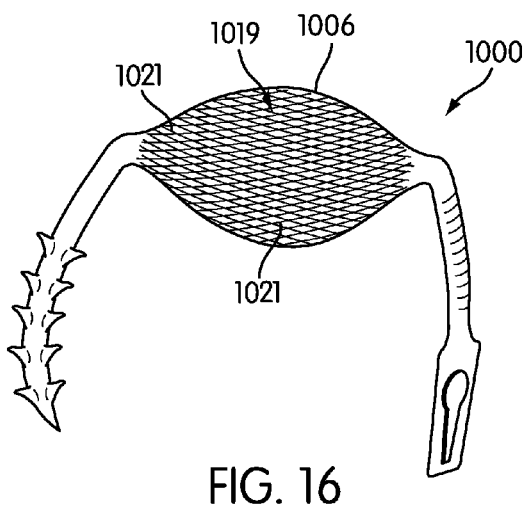
FIG. 16 is a perspective view of a further embodiment of a prosthesis.
Figure 17:
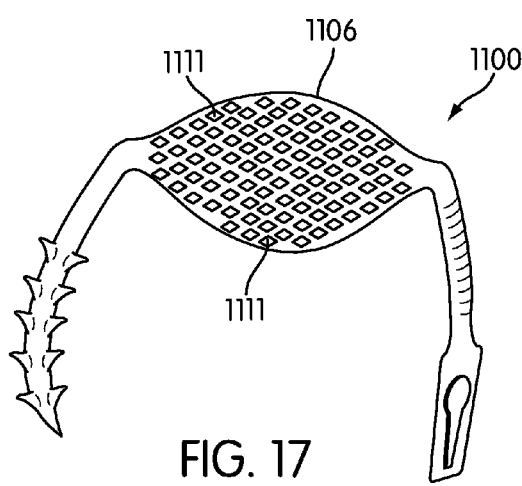
FIG. 17 is a perspective view of yet another embodiment of a prosthesis.

FIGS. 15-17 illustrate embodiments of prostheses having various features related to their intermediate portions, which can provide benefits depending on factors such as intended use of the devices, types of tissues involved, insertion location, anticipated stresses at the insertion site, etc. FIG. 15 shows prosthesis 900 having a flat intermediate portion 906, which has a width W greater than its thickness. Such a configuration can allow prosthesis 900 to have a generally constant cross-sectional area along most of its length along with a changing area moment of inertia based on the flat geometry of the intermediate portion. This can provide a prosthesis 900 that maintains a substantially uniform tensile strength along its length by generally maintaining its cross-sectional area, while changing its geometry to provide features that could beneficial in some cases. The flat geometry of the intermediate portion can provide a low profile and can favor bending along axes within a plane generally parallel to the flat region. For instance, prosthesis 900 can favor bending along transverse axes extending across the width W.

The configuration of prosthesis 900 can provide advantages for particular uses and insertion locations. For example, flat intermediate portion 906 can be beneficial for uses in which a low profile of the intermediate portion would be desirable, such as when disposed between translating tissues or within a tight space. Prosthesis 900 and thin intermediate portion 906 could provide benefits when placed at a spinal disk such that intermediate portion 906 would be disposed at an outer portion of the disk.

In addition, intermediate portion 906 can have various surface textures to provide particular features. For instance, outer surface 915 of intermediate portion 906 could be smooth to avoid irritating adjacent tissues that are expected to translate or otherwise move relative to the prosthesis during body movements. In other cases, outer surface 915 could have another texture, such as a rough texture that can enhance fit of the prosthesis with adjacent tissues. Inner surface 917 can also have other textures that can provided particular benefits, such as contours similar to nearby tissues, textures designed to encourage particular physiological responses in nearby tissues, or textures designed to adhere with adjacent tissues. In addition, inner and outer surfaces 915 and 917 can have geometric features, such as projections, nubs, and fastening features like hooks or loops, etc. As shown in FIG. 15, inner surface 915 and/or outer surface 917 can have flat angular projections 907 extending therefrom, which can be generally triangular shaped. These projections can act like small hooks or barbs 907 to attach the intermediate portion 906 to adjacent tissue.

FIG. 16 is a perspective view of a further embodiment of prosthesis 1000, which generally includes the aspects and features of prosthesis 900 except as discussed hereafter. As shown, prosthesis 1000 can include a mesh 1019 of reinforcing fibers 1021 at intermediate portion 1006. Such a configuration can provide an even thinner cross-sectional area for intermediate portion 1006 while maintaining a desired tensile strength. Reinforcing fibers 1021 can be embedded in a substrate used to form the prosthesis, such as materials described above along with FIG. 1A for forming the prosthesis including suture materials or plastic materials. The fibers can also be attached to portions of the prosthesis via an adhesive or a mechanical attachment.

The reinforcing fibers can be made of the same types of materials noted above along with FIG. 1A for the prosthesis, but would preferably have different material properties than other materials used to form the prosthesis, such as having a greater tensile strength or better flexibility than a base material. In some cases, reinforcing fibers can be used at other portions of prosthesis 1000 or throughout the device to provide particular features and configurations of prostheses having desired benefits for particular uses. In other cases, reinforcing fibers can be used alone at portions of prosthesis 1000, which can provide benefits such as an even thinner profile with greater bending characteristics, the ability to merge with adjacent soft tissues, or to provide fluid absorption or flow characteristics by the mesh of fibers.

FIG. 17 is a perspective view of a further embodiment of prosthesis 1100, which generally includes the aspects and features of prosthesis 900 except as discussed hereafter. As shown, prosthesis 1100 can include an arrangement of openings 1111 within intermediate portion 1106. Such a configuration can provide improved properties at the intermediate portion, such as greater longitudinal elongation, elasticity, and bending. For instance, it can be desirable for some uses to have a very elastic prosthesis 1100 during insertion that can be substantially elongated as needed during insertion. In addition, the openings could be beneficial to permit the flow of fluids through the intermediate portion. Intermediate portion 1106 can be formed with the openings 1111, such as being molded in a prosthesis made from a thermoplastic material. In addition, openings 1111 can be made in the prosthesis as a later operation, such as being punched, cut or otherwise created in the prosthesis. Openings 1111 can have various shapes, sizes and arrangements to provide desired benefits, such as diamond shapes as shown in FIG. 17, or rounded shapes including circles or ovals, etc.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A method of implanting a prosthesis comprising:
delivering a first end portion and a second end portion of a prosthesis on a distal portion of a tissue, wherein the distal portion is disposed farther from a surgeon than a proximal portion of the tissue;
wherein delivering the first end portion and the second end portion comprises
inserting a first delivery needle containing the first end portion through the proximal portion of the tissue and passing the first delivery needle through the tissue and to the distal portion of the tissue, and
inserting a second delivery needle containing the second end portion through the proximal portion of the tissue and passing the second delivery needle through the tissue and to the distal portion of the tissue;
delivering an intermediate portion of the prosthesis to the proximal portion of the tissue; and
fastening the first end portion to the second end portion by moving the first delivery needle and the second delivery needle toward each other at the distal portion of the tissue such that a first delivery direction provided by the first delivery needle crosses a second delivery direction provided the second delivery needle and the first end portion crosses and connects with the second end portion,
wherein in a pre-actuated condition a first needle end of the first delivery needle and a second needle end of the second delivery needle extend substantially equal distances in a distal direction, and
wherein in moving the first delivery needle and the second delivery needle toward each other, the second needle end extends distally farther than the first needle end.

2. The method according to claim 1, wherein delivering the first end portion and the second end portion of the prosthesis includes associating a delivery device with the tissue, wherein the delivery device includes the first delivery needle and the second delivery needle.

3. The method according to claim 2, wherein a portion of the delivery device is disposed within a cannula.

4. The method according to claim 2, wherein fastening is followed by removing the delivery device.

5. The method according to claim 1, wherein the second delivery needle defines an opening facing transverse to the second delivery direction of the second delivery needle, and wherein moving the first delivery needle and the second delivery needle toward each other points the first delivery direction of the first delivery needle through the opening.

6. The method according to claim 5, further comprising moving the first delivery needle through the opening of the second delivery needle.

7. The method according to claim 1, wherein the tissue has a first proximal side and a second distal side,
wherein delivering the first end portion and the second end portion of the prosthesis comprises inserting the first end portion and the second end portion through the first proximal side and passing the first end portion and the second end portion through the tissue so that the first end portion and the second end portion emerge on the second distal side of the tissue, and wherein fastening the first end portion to the second end portion comprises fastening the first end portion to the second end portion outside of the tissue on the second distal side of the tissue.

8. The method according to claim 7, wherein the tissue comprises a first tissue portion and a second tissue portion separated from the first tissue portion by a gap, wherein delivering the first end portion on the distal portion of the tissue comprises inserting the first end portion through a first proximal side of the first tissue portion and passing the first end portion through the first tissue portion so that the first end portion emerges on a second distal side of the first tissue portion, wherein delivering the second end portion on a distal portion of the tissue comprises inserting the second end portion through a first proximal side of the second tissue portion and passing the second end portion through the second tissue portion so that the second end portion emerges on a second distal side of the second tissue portion, wherein delivering the intermediate portion comprises positioning the intermediate portion such that the intermediate portion spans the gap separating the first tissue portion from the second tissue portion, and wherein fastening the first end portion to the second end portion comprises fastening the first end portion to the second end portion across the gap separating the first tissue portion from the second tissue portion so that the first tissue portion and the second tissue portion are pulled closer together.

9. The method according to claim 8, wherein the intermediate portion on the proximal side of the tissue has a first geometric feature facing the first tissue portion and a second geometric feature facing the second tissue portion, wherein the method further comprises attaching the intermediate portion to the first tissue portion using the first geometric feature and to the second tissue portion using the second geometric feature.

10. The method according to claim 9, wherein each of the first geometric feature and the second geometric feature comprises at least one of at least one projection, at least one nub, at least one hook, at least one loop, and at least one barb.

11. The method according to claim 1, wherein moving the first delivery needle and the second delivery needle toward each other comprises moving the first delivery needle and the second delivery needle against forces biasing the first delivery needle and the second delivery needle away from each other.

12. The method according to claim 11, wherein a connector is connected to the first delivery needle and the second delivery needle, wherein the connector extends laterally between the first delivery needle and the second delivery needle, and wherein moving the first delivery needle and the second delivery needle toward each other comprises moving the first delivery needle and the second delivery needle against forces of the connector biasing the first delivery needle and the second delivery needle away from each other.

13. The method according to claim 1, wherein the delivery device further comprises an actuator connected to the first delivery needle and the second delivery needle, and wherein fastening the first end portion to the second end portion comprises applying a first force to the actuator in a retraction direction opposite to an implantation direction such that the actuator converts the first force into a second force that moves the first delivery needle toward the second delivery needle and into a third force that moves the second delivery needle toward the first delivery needle.

14. A method of implanting a prosthesis comprising:

delivering a first end portion and a second end portion of a prosthesis on a distal portion of a tissue, wherein the distal portion is disposed farther from a surgeon than a proximal portion of the tissue:

wherein delivering the first end portion and the second end portion comprises inserting a first delivery needle containing the first end portion through the proximal portion of the tissue and passing the first delivery needle through the tissue and to the distal portion of the tissue, and inserting a second delivery needle containing the second end portion through the proximal portion of the tissue and passing the second delivery needle through the tissue and to the distal portion of the tissue:

delivering an intermediate portion of the prosthesis to the proximal portion of the tissue; and fastening the first end portion to the second end portion by moving the first delivery needle and the second delivery needle toward each other at the distal portion of the tissue such that a first delivery direction provided by the first delivery needle crosses a second delivery direction provided the second delivery needle and the first end portion crosses and connects with the second end portion, wherein the second delivery needle defines an opening facing transverse to the second delivery direction of the second delivery needle, and wherein moving the first delivery needle and the second delivery needle toward each other points the first delivery direction of the first delivery needle through the opening, and wherein the second end portion defines a receiving portion, and wherein the method further comprises pushing the first end portion through the receiving portion, beyond an intersection of the crossing first and second end portions, through the opening of the second delivery needle, and beyond the second delivery needle in the first delivery direction.

15. A method of implanting a prosthesis comprising:

delivering a first end portion and a second end portion of a prosthesis on a distal portion of a tissue, wherein the distal portion is disposed farther from a surgeon than a proximal portion of the tissue;

wherein delivering the first end portion and the second end portion comprises inserting a first delivery needle containing the first end portion through the proximal portion of the tissue and passing the first delivery needle through the tissue and to the distal portion of the tissue, and inserting a second delivery needle containing the second end portion through the proximal portion of the tissue and passing the second delivery needle through the tissue and to the distal portion of the tissue;

delivering an intermediate portion of the prosthesis to the proximal portion of the tissue; and fastening the first end portion to the second end portion by moving the first delivery needle and the second delivery needle toward each other at the distal portion of the tissue such that a first delivery direction provided by the first delivery needle crosses a second delivery direction provided the second delivery needle and the first end portion crosses and connects with the second end portion, wherein fastening the first end portion to the second end portion includes applying a force to a pushing member that pushes the first end portion of the prosthesis in the first delivery direction and beyond an intersection between the crossing first and second end portions.

16. A method of implanting a prosthesis comprising:
delivering a first end portion and a second end portion of a prosthesis on a distal portion of a tissue, wherein the distal portion is disposed farther from a surgeon than a proximal portion of the tissue;
wherein delivering the first end portion and the second end portion comprises
inserting a first delivery needle containing the first end portion through the proximal portion of the tissue and passing the first delivery needle through the tissue and to the distal portion of the tissue, and
inserting a second delivery needle containing the second end portion through the proximal portion of the tissue and passing the second delivery needle through the tissue and to the distal portion of the tissue;
delivering an intermediate portion of the prosthesis to the proximal portion of the tissue; and
fastening the first end portion to the second end portion by moving the first delivery needle and the second delivery needle toward each other at the distal portion of the tissue such that a first delivery direction provided by the first delivery needle crosses a second delivery direction provided the second delivery needle and the first end portion crosses and connects with the second end portion,
wherein the second delivery needle defines an opening facing transverse to the second delivery direction of the second delivery needle, and wherein moving the first delivery needle and the second delivery needle toward each other points the first delivery direction of the first delivery needle through the opening, and
wherein the opening comprises an open ended slot formed between two members at a distal end of the second delivery needle.

17. A method of implanting a prosthesis comprising:
delivering a first end portion and a second end portion of a prosthesis on a distal portion of a tissue, wherein the distal portion is disposed farther from a surgeon than a proximal portion of the tissue;
delivering an intermediate portion of the prosthesis to the proximal portion of the tissue; and
fastening the first end portion to the second end portion,
wherein delivering the first end portion and the second end portion of the prosthesis includes associating a delivery device with the tissue,
wherein the delivery device comprises:
a first delivery needle and a second delivery needle that are configured to penetrate through to the distal portion of the tissue in an implantation direction, wherein the first delivery needle and the second delivery needle extend in a longitudinal direction, wherein a first needle end of the first delivery needle and a second needle end of the second delivery needle are spaced laterally apart from each other when in a pre-actuated condition, and wherein the first needle end is associated with the first end portion and the second needle end is associated with the second end portion, and
an actuator connected to the first delivery needle and the second delivery needle, and
wherein delivering the first end portion and the second end portion on the distal portion of the tissue comprises:
applying a first force to the actuator in a retraction direction opposite to the implantation direction such that the actuator converts the first force into a second force that moves the first needle end toward the second needle end and into a third force that moves the second needle end toward the first needle end,
wherein the actuator comprises:
a tensioning member extending in the longitudinal direction and having a distal end portion disposed closest to the first and second needle ends and a proximal end portion disposed farthest from the first and second needle ends,
a first actuator link having a first link end portion and a second link end portion opposite to the first link end portion, wherein the first link end portion is pivotably connected to the distal end portion of the tensioning member and the second link end portion is pivotably connected to the first delivery needle,
a second actuator link having a third link end portion and a fourth link end portion opposite to the third link end portion, wherein the third link end portion is pivotably connected to the distal end portion of the tensioning member and the fourth link end portion is pivotably connected to the second delivery needle,
wherein applying the first force to the tensioning member in the retraction direction comprises:
the tensioning member pulling the first link end portion of the first actuator link and the third link end portion of the second actuator link in the retraction direction,
the second link end portion of the first actuator link pulling the first delivery needle toward the second delivery needle,
the fourth link end portion of the second actuator link pulling the second delivery needle toward the first delivery needle, and
thereby moving the first needle end of the first delivery needle and the second needle end of the second delivery needle toward each other;
wherein the delivery device further comprises a connector that is connected at a first pivot point to a first intermediate portion of the first delivery needle and is connected at a second pivot point to a second intermediate portion of the second delivery needle,
wherein the connector extends laterally between the first delivery needle and the second delivery needle,
wherein the second link end portion of the first actuator link is pivotably connected to the first delivery needle at a first pivot and the fourth link end portion of the second actuator link is pivotably connected to the second delivery needle at a second pivot,
wherein the first and second needle ends are disposed on a first side of the first and second pivots, and
wherein the connector is disposed on a second side of the first and second pivots opposite to the first side of the first and second pivots, such that the connector holds the first and second delivery needles in the laterally spaced apart pre-actuated condition and against the second and third forces,
wherein delivering the first end portion and the second end portion further comprises:
pivoting the first delivery needle with respect to the first pivot point to move the first needle end toward the second needle end, and
pivoting the second delivery needle with respect to the second pivot point to move the second needle end toward the first needle end, and wherein the method further comprises using the connector to
    hold the first and second delivery needles in the laterally spaced apart pre-actuated condition,
    oppose the second and third forces when the first force is applied to the actuator, and
    return the first and second delivery needles to the laterally spaced apart pre-actuated condition when the first force is removed.

18. A method of implanting a prosthesis into a tissue having a distal portion and a proximal portion, the distal portion being disposed farther from a surgeon than the proximal portion, the method comprising:
    holding a first end portion of the prosthesis in a first needle end of a first delivery needle;
    holding a second end portion of the prosthesis in a second needle end of a second delivery needle, wherein the first delivery needle and the second delivery needle are held laterally spaced apart from each other in a pre-actuated condition by a connector extending laterally between the first delivery needle and the second delivery needle, and wherein the prosthesis has an intermediate portion that is between the first end portion and the second end portion and extends between the first delivery needle and the second delivery needle in the pre-actuated condition;
    inserting the first end portion and the second end portion of the prosthesis into the tissue using the first delivery needle and the second delivery needle, respectively;
    actuating a tensioning member that moves the first delivery needle and the second delivery needle toward each other and against an opposing force of the connector, such that the first needle end of the first delivery needle guides the first end portion in a first delivery direction and the second needle end of the second delivery needle guides the second end portion in a second delivery direction, wherein the first delivery direction crosses the second delivery direction;
    pushing the first end portion within the second needle end and along the first delivery direction such that the first end portion crosses the second end portion and engages the second end portion at the distal portion of the tissue, with the intermediate portion at the proximal portion of the tissue; and
    releasing the tensioning member so that the opposing force of the connector returns the first delivery needle and the second delivery needle to the pre-actuated condition,
    wherein in the pre-actuated condition a first needle end of the first delivery needle and a second needle end of the second delivery needle extend substantially equal distances in a distal direction, and
    wherein actuating the tension member positions the second needle end distally farther than the first needle end.

19. The method according to claim 18, wherein the second delivery needle defines an opening facing transverse to the second delivery direction of the second delivery needle,
    wherein moving the first delivery needle and the second delivery needle toward each other points the first delivery direction of the first delivery needle through the opening,
    wherein the second end portion defines a receiving portion, and
    wherein the method further comprises pushing the first end portion through the receiving portion, beyond an intersection of the crossing first and second end portions, through the opening of the second delivery needle, and beyond the second delivery needle in the first delivery direction.

20. A method of implanting a prosthesis into a tissue having a distal portion and a proximal portion, the distal portion being disposed farther from a surgeon than the proximal portion, the method comprising:
    holding a first end portion of the prosthesis in a channel of a first delivery needle;
    holding a second end portion of the prosthesis in a second delivery needle, wherein the first delivery needle and the second delivery needle are laterally spaced apart from each other in a pre-actuated condition, and wherein the prosthesis has an intermediate portion that is between the first end portion and the second end portion and extends between the first delivery needle and the second delivery needle in the pre-actuated condition;
    inserting the first end portion and the second end portion of the prosthesis into the tissue using the first delivery needle and the second delivery needle, respectively;
    moving the first delivery needle and the second delivery needle toward each other such that the channel of the first delivery needle is aligned to guide the first end portion of the prosthesis in a first delivery direction and the second delivery needle is aligned to guide the second end portion of the prosthesis in a second delivery direction, wherein the first delivery direction crosses the second delivery direction; and
    pushing the first end portion of the prosthesis with a pushing member disposed in the channel of the first delivery needle so that the first end portion crosses the second end portion and engages the second end portion at the distal portion of the tissue, with the intermediate portion at the proximal portion of the tissue,
    wherein in a pre-actuated condition a first needle end of the first delivery needle and a second needle end of the second delivery needle extend substantially eaual distances in a distal direction, and
    wherein in moving the first delivery needle and the second delivery needle toward each other, the second needle end extends distally farther than the first needle end.

21. The method according to claim 20, wherein the second delivery needle defines an opening facing transverse to the second delivery direction of the second delivery needle,
    wherein moving the first delivery needle and the second delivery needle toward each other points the first delivery direction of the first delivery needle through the opening, and
    wherein the second end portion defines a receiving portion, and
    wherein the method further comprises pushing the first end portion through the receiving portion beyond an intersection of the crossing first and second end portions, through the opening of the second delivery needle, and beyond the second delivery needle in the first delivery direction.

22. A method of implanting a prosthesis comprising:
    delivering a first end portion and a second end portion of a prosthesis on a distal portion of a tissue, wherein the distal portion is disposed farther from a surgeon than a proximal portion of the tissue;
    wherein delivering the first end portion and the second end portion comprises
        inserting a first delivery needle containing the first end portion through the proximal portion of the tissue and passing the first delivery needle through the tissue and to the distal portion of the tissue, and
        inserting a second delivery needle containing the second end portion through the proximal portion of the tissue and passing the second delivery needle through the tissue and to the distal portion of the tissue;

delivering an intermediate portion of the prosthesis to the proximal portion of the tissue; and fastening the first end portion to the second end portion by moving the first delivery needle and the second delivery needle toward each other at the distal portion of the tissue such that a first delivery direction provided by the first delivery needle crosses a second delivery direction provided the second delivery needle and the first end portion crosses and connects with the second end portion, wherein the first delivery needle has a first linear proximal portion and a first curved distal portion and the second delivery needle has a second linear proximal portion and a second curved distal portion, wherein the first curved distal portion guides the first end portion in the first delivery direction, and wherein the second curved distal portion guides the second end portion in the second delivery direction.

23. The method according to claim 22, wherein the first delivery needle has a first pushing member in the first linear proximal portion, and wherein the method further comprises using the first pushing member to push the first end portion of the prosthesis along the first curved distal portion in the first delivery direction to intersect the second end portion.

24. The method according to claim 23, wherein the second delivery needle has a second pushing member in the second linear proximal portion, and wherein the method further comprises using the second pushing member to convey a force to the second end portion of the prosthesis to assist the second end portion in fastening to the first end portion.

* * * * *